US009856458B2

(12) United States Patent
Rosowski et al.

(10) Patent No.: US 9,856,458 B2
(45) Date of Patent: Jan. 2, 2018

(54) 3D IN VITRO BI-PHASIC CARTILAGE-BONE CONSTRUCT

(71) Applicant: TISSUSE GMBH, Berlin (DE)

(72) Inventors: Mark Rosowski, Berlin (DE); Shirin Kadler, Berlin (DE); Roland Lauster, Berlin (DE); Uwe Marx, Spreenhagen (DE)

(73) Assignee: TISSUSE GMBH, Berlin (DE)

( * ) Notice: Subject to any disclaimer, the term of this patent is extended or adjusted under 35 U.S.C. 154(b) by 0 days.

(21) Appl. No.: 14/381,216

(22) PCT Filed: Feb. 28, 2013

(86) PCT No.: PCT/EP2013/054030
§ 371 (c)(1),
(2) Date: Aug. 27, 2014

(87) PCT Pub. No.: WO2013/127921
PCT Pub. Date: Sep. 6, 2013

(65) Prior Publication Data
US 2015/0093428 A1  Apr. 2, 2015

(30) Foreign Application Priority Data
Feb. 29, 2012  (EP) .................................. 12157484

(51) Int. Cl.
*C12N 5/0775* (2010.01)
*C12N 5/071* (2010.01)
*C12N 5/0789* (2010.01)
*C12N 5/077* (2010.01)
*G01N 33/50* (2006.01)
*G01N 33/68* (2006.01)
*A61L 27/10* (2006.01)
*A61L 27/38* (2006.01)
*A61L 27/50* (2006.01)
*A61L 27/54* (2006.01)
*C12M 3/00* (2006.01)
*C12M 1/00* (2006.01)

(52) U.S. Cl.
CPC ............ *C12N 5/0697* (2013.01); *A61L 27/10* (2013.01); *A61L 27/3834* (2013.01); *A61L 27/3847* (2013.01); *A61L 27/3852* (2013.01); *A61L 27/50* (2013.01); *A61L 27/54* (2013.01); *C12M 21/08* (2013.01); *C12M 29/00* (2013.01); *C12N 5/0647* (2013.01); *C12N 5/0655* (2013.01); *C12N 5/0663* (2013.01); *G01N 33/502* (2013.01); *G01N 33/5044* (2013.01); *G01N 33/5088* (2013.01); *G01N 33/6887* (2013.01); *A61L 2300/64* (2013.01); *A61L 2430/02* (2013.01); *A61L 2430/06* (2013.01); *C12N 2502/1171* (2013.01); *C12N 2502/1311* (2013.01); *C12N 2502/1317* (2013.01); *C12N 2502/1358* (2013.01); *C12N 2506/1353* (2013.01); *C12N 2513/00* (2013.01); *C12N 2533/14* (2013.01)

(58) Field of Classification Search
None
See application file for complete search history.

(56) References Cited

U.S. PATENT DOCUMENTS

2007/0123996 A1\* 5/2007 Sugaya ................. A61L 27/047
 623/23.51
2011/0086382 A1   4/2011 Marx
2011/0274729 A1\* 11/2011 Collins ................... A61L 27/34
 424/400
2013/0295598 A1   11/2013 Marx et al.

FOREIGN PATENT DOCUMENTS

EP      10 008 244       8/2010
WO   WO 2009/146911 A2  12/2009
WO   WO 2012/016711 A1   2/2012

OTHER PUBLICATIONS

Wiegandt, Katharina, Christiane Goepfert, and Ralf Pörtner. "Improving in vitro generated cartilage-carrier-constructs by optimizing growth factor combination." The open biomedical engineering journal 1.1:85-90 (2007).\*
Piera-Velazquez, Sonsoles, Sergio A. Jimenez, and David G. Stokes. "Increased life span of human osteoarthritic chondrocytes by exogenous expression of telomerase." Arthritis & Rheumatism 46.3 (2002): 683-693.\*
K. Wiegandt et al.: "Improving In Vitro Generated Cartilage-Carrier-Constructs by Optimizing Growth Factor Combination", The Open Biomedical Engineering Journal, vol. 1, pp. 85-90 (2007).
S. Piera-Velazquez et al.: "Increased Life Span of Human Osteoarthritic Chondrocytes by Exogenous Expression of Telomerase", Arthritis & Rheumatism, vol. 46, No. 3, pp. 683-693 (Mar. 2002).
M. Rosowski et al.: "Initiation of Mesenchymal Condensation in Alginate Hollow Spheres—A useful Model for Understanding Cartilage Repair?", Artificial Organs, vol. 30, No. 10, pp. 775-784 (2006).
I. Martin et al.: "Osteochondral tissue engineering", Journal of Biomechanics, vol. 40, pp. 750-765 (2007).
J. Tan et al.: "Maintenance and expansion of hematopoietic stem/progenitor cells in biomimetic osteoblast niche", Cytotechnology, vol. 62, pp. 439-448 (2010).
F. Tortelli et al.: "Three-Dimensional Cultures of Osteogenic and Chondrogenic Cells: A Tissue Engineering Approach to Mimic Bone and Cartilage In Vitro", European Cells and Materials, vol. 17, pp. 1-14 (2009).

(Continued)

*Primary Examiner* — Robert Yamasaki
(74) *Attorney, Agent, or Firm* — Norman B. Thot

(57) ABSTRACT

A 3D in vitro bi-phasic cartilage-bone organoid includes a layer of an artificial cartilage tissue, and a layer of an artificial bone tissue comprising a structure-giving scaffold and a bone marrow structure. The layer of the artificial cartilage tissue contacts at least one surface of the layer of the artificial bone tissue.

7 Claims, 17 Drawing Sheets

(56) References Cited

OTHER PUBLICATIONS

M. Baker: "Technology Feature: A Living System on a Chip", Nature, vol. 471, pp. 661-665 (Mar. 31, 2011).
U. Marx: "BMBF Go-Bio project: From single tissue culture to multi-organ-chips", AXLR8 satellite meeting, Berlin, presentation, pp. 1-18 (May 22, 2011).
J. L. Olson et al.: "Tissue Engineering: Current Strategies and Future Directions", Chonnam Medical Journal, vol. 47, pp. 1-13 (2011).
A. Papadimitripoulos et al.: "A 3D In Vitro Bone Organ Model Using Human Progenitor Cells", European Cells and Materials, vol. 21, pp. 445-458 (2011).

\* cited by examiner

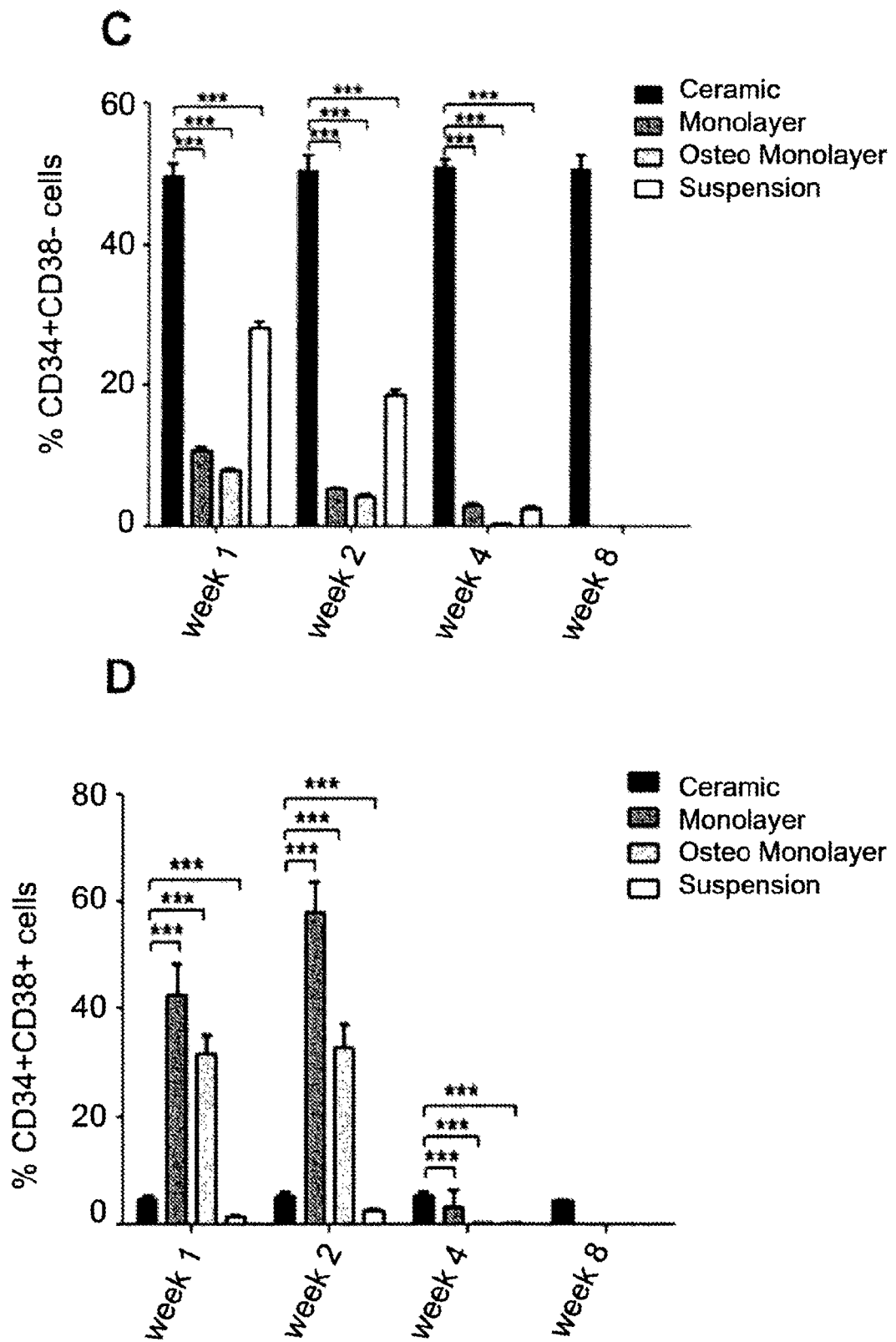
Fig. 10C-D

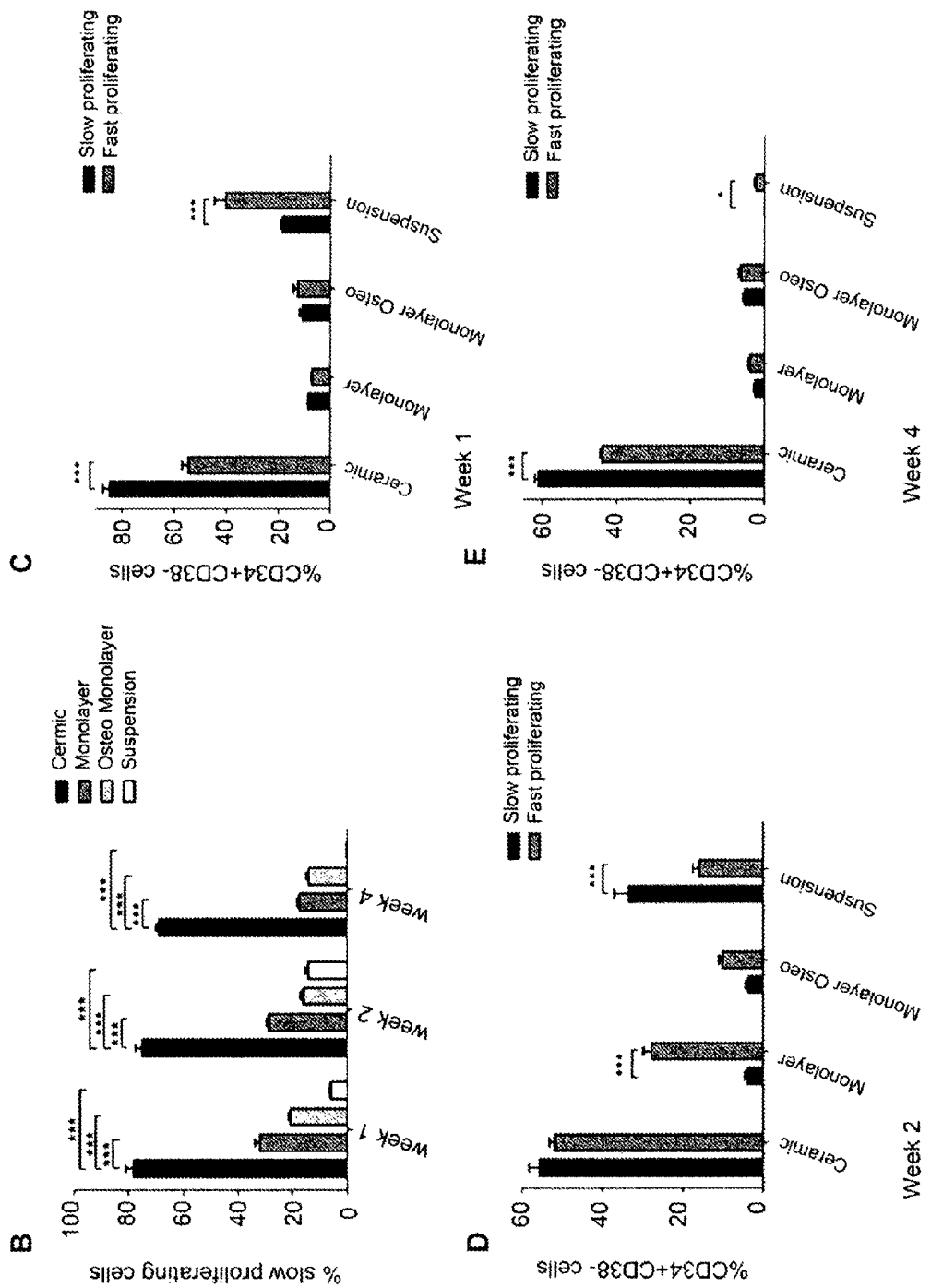
Fig. 11B-E

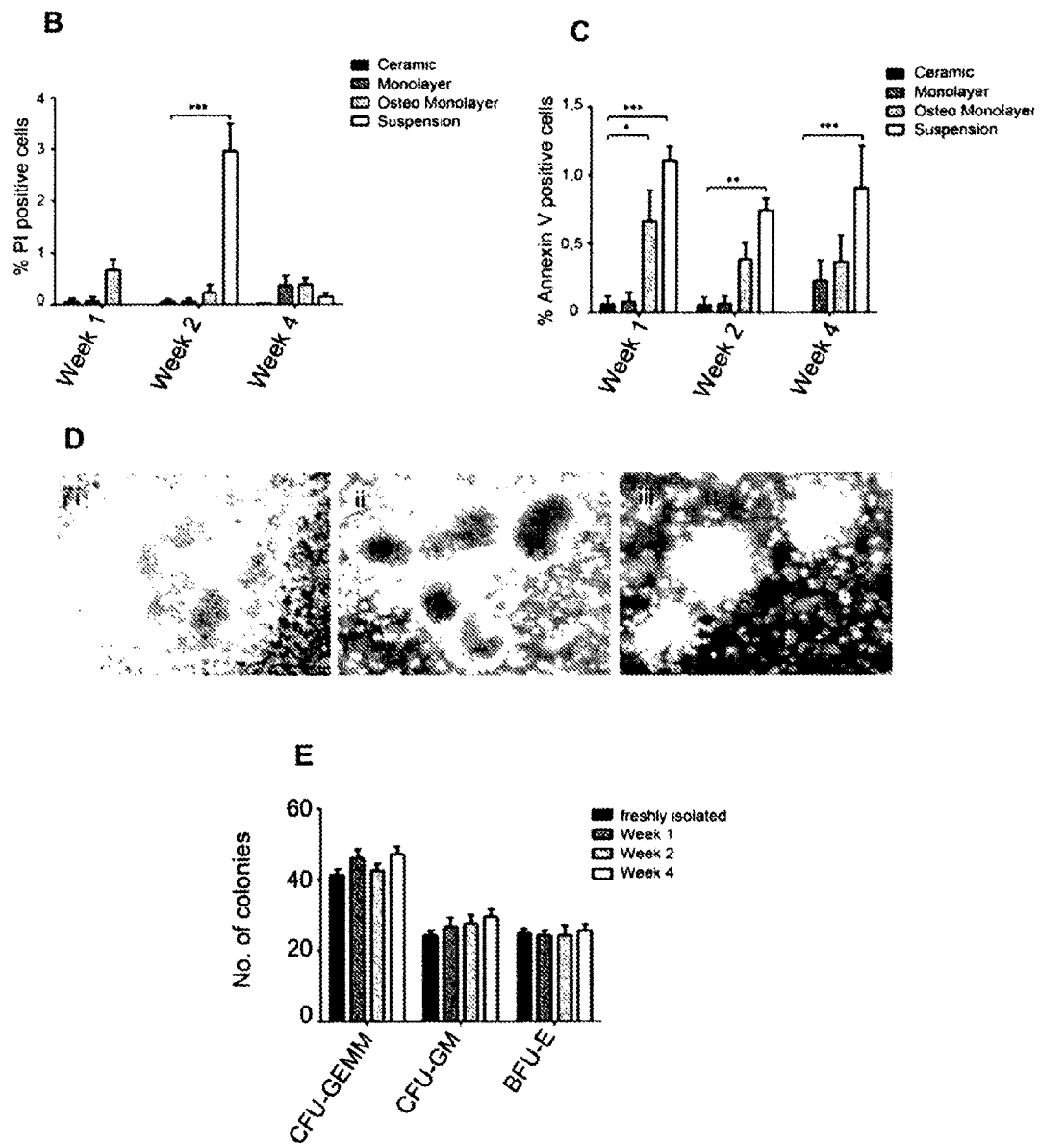
Fig. 12B-E

3D IN VITRO BI-PHASIC CARTILAGE-BONE CONSTRUCT

CROSS REFERENCE TO PRIOR APPLICATIONS

This application is a U.S. National Phase application under 35 U.S.C. §371 of International Application No. PCT/EP2013/054030, filed on Feb. 28, 2013 and which claims benefit to European Patent Application No. 12157484.2, filed on Feb. 29, 2012. The International Application was published in English on Sep. 6, 2013 as WO 2013/127921 A1 under PCT Article 21(2).

FIELD

The present invention relates to a 3D in vitro bi-phasic cartilage-bone organoid comprising: a) a layer of artificial cartilage tissue; and b) a layer of artificial bone tissue, wherein the artificial bone tissue comprises a structure-giving scaffold and a bone marrow structure; wherein the layer of artificial cartilage tissue contacts at least one surface of the layer of artificial bone tissue, as well as to uses and a method of production thereof.

BACKGROUND

Numerous diseases are associated with degenerative changes in joint cartilage or misguided differentiation processes in bone marrow. Diseases of the muscle-skeletal system represent the third most cost intensive factor in treatment of diseases in Germany, after diseases of the cardio vascular system and diseases of the digestive system. One of the prerequisites for successful treatment of such diseases is the understanding of the cellular processes in the bone marrow that underlie these diseases or are associated therewith. So it is possible to treat e.g., leukaemia by replacement of the hematopoietic system of a patient. Also autoimmune diseases, like rheumatoid arthritis or lupus erythematodes, are, however, regulated by long-lived plasma and memory-T-cells which reside in specialized niches of the bone marrow.

The bone marrow is a multi-functional, multi-cellular tissue which, inter alia, is located in the lumen of long bones. The tissue develops during the embryonic development around month 4, in the context of the endochondral ossification, the development of the long bones. The bone marrow is characterized by a porous structure formed of cancellous bone and specialized connective tissue pervaded with numerous thin-walled blood vessels, the bone marrow sinusoids. One of the main functions of the bone marrow is the provision of a suitable environment for differentiation of the blood forming cells of the hematopoietic system. The hematopoietic stem cell (HSC) represents the starting point for these differentiation processes, wherein the hematopoietic stem cell resides in undifferentiated state in the hematopoietic stem cell niches in the cancellous bone structures of the bone marrow. The hematopoietic stem cell niches are divided in two functionally different subtypes. In the osteoblast-niche, the hematopoietic HSCs interact with specialized osteoblasts via different adhesion and signalling molecules whereby the HSCs are kept in a rounded, non-proliferating state. Upon mobilisation of HSCs, the stem cells migrate to the vascular stem cell niches located at the sinusoids where the HSCs exhibit increased proliferation. According to today's understanding of hematopoietic stem cell niches in bone marrow, the smallest unit of a stem cell niche system is formed of a combination of an osteoblast niche and a vascular niche located at a sinusoid blood vessel of cancellous bone. Apart from the functional structures of the stem cell niches, current research discloses bone marrow as home of the immunologic memory. Mesenchymal stroma cells (MSC) serve as cellular building blocks of survival niches for plasma and memory-T-cells. In summary, the biological functionality of the bone marrow depends on a number of cells like HSC, MSC, endothelial cells and osteoblasts and their proper interaction in the spatial compartment.

Hyaline cartilage of the joints, due to its properties of a high elasticity to pressure and a very even surface, allows for a friction-poor movement of the joints. The main part of this tissue is formed of a plurality of extracellular matrix proteins, whereas the cellular component, the chondrocytes, is embedded sparsely in this matrix either separately or in small groups (chondron). The lack of nerve fibres and blood vessels and the resulting low supply of the tissue with oxygen and nutrients generate a unique micro-environment for the chondrocytes. The cartilage tissue can be classified in multiple layers, wherein, due to the horizontal orientation of the matrix molecules, the uppermost layer can counteract friction and, due to the vertical orientation, the subjacent middle and lower layers can absorb impact force originating from movement. Although chondrocytes emerge early during endochondral ossification of the initial process of mesenchymal condensation and these cells contribute significantly to bone growth during epiphysis, the hyaline cartilage tissue in the joint develops only at a very late point in time during embryogenesis. Fully differentiated, fully functional layers of cartilage are formed only postnatal by beginning mechanical stimulation of the tissue. In the adult organism, homeostasis of cartilage tissue is highly dependent of the kind and strength of mechanic load and of the micro-environment of the embedded chondrocytes.

Numerous attempts have been made to develop and provide in vitro models and test systems for bone and cartilage tissue. These approaches are, however, directed either to the separated provision of bone or cartilage tissue. These models thus do represent the natural environment only partially and insufficiently in which development and homeostasis of bone, bone marrow and cartilage tissue takes place.

SUMMARY

An aspect of the present invention is to overcome one or more problems of the prior art.

In an embodiment, the present invention provides a 3D in vitro bi-phasic cartilage-bone organoid which includes a layer of an artificial cartilage tissue, and a layer of an artificial bone tissue comprising a structure-giving scaffold and a bone marrow structure. The layer of the artificial cartilage tissue contacts at least one surface of the layer of the artificial bone tissue.

BRIEF DESCRIPTION OF THE DRAWINGS

The present invention is described in greater detail below on the basis of embodiments and of the drawings in which.

DETAILED DESCRIPTION

Figure 1A:
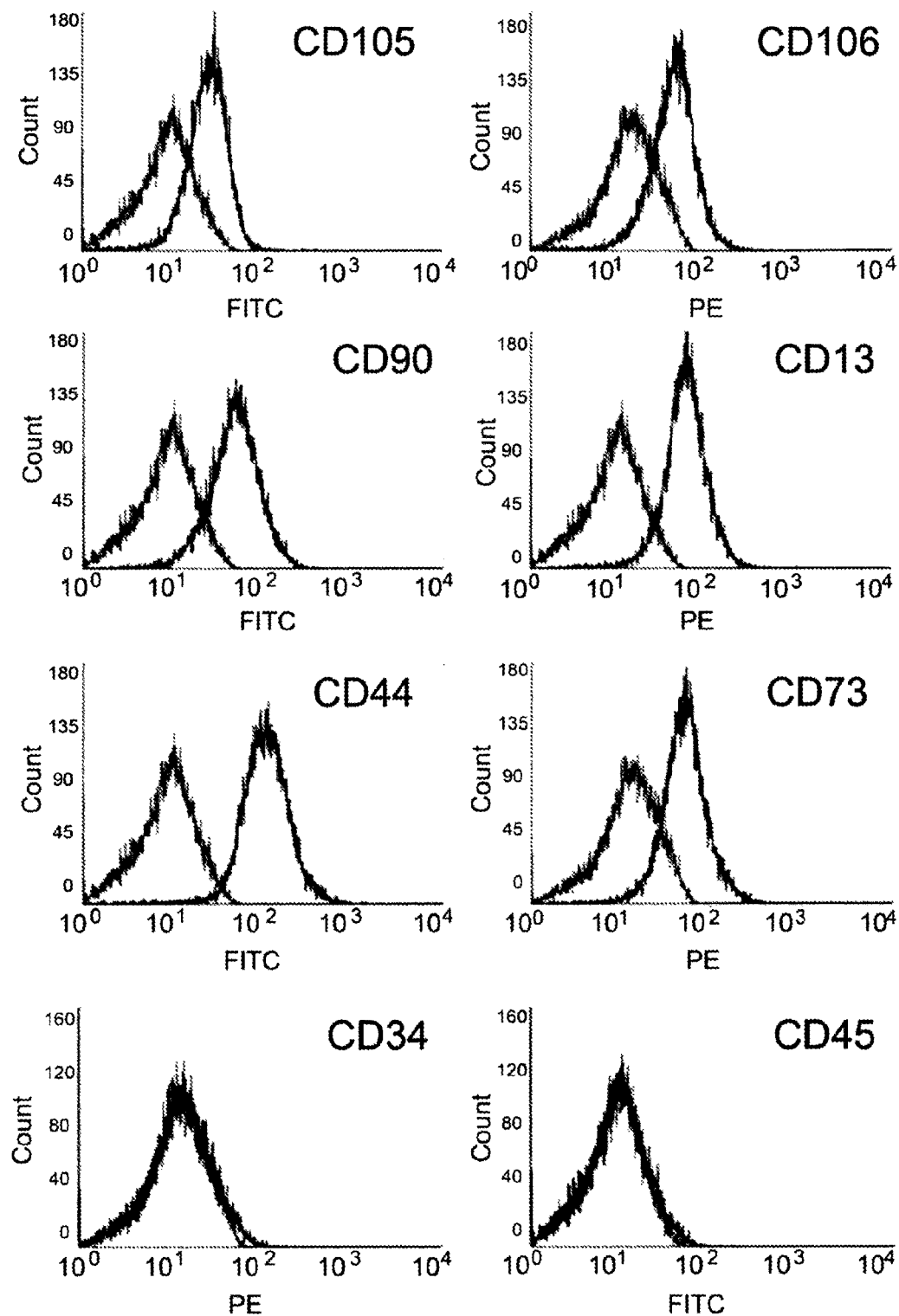
FIG. 1 shows that dedifferentiated chondrocytes display mesenchymal stem cell character. [A] Dedifferentiated chondrocytes were stained for the mesenchymal surface marker panel. The cells were positive for CD105, CD106, CD44, CD73, CD90 and CD13 and negative for the hematopoietic markers CD34 and CD45 (one representative experiment is shown, n=6). Adipogenic differentiation. [B-D] Dedifferentiated chondrocytes were treated with adipogenic medium for 28 days. Adipocyte differentiation was evaluated by light microscopy and Oil-Red-O-staining. B) negative control of monolayer cells, unstained; C) negative control of monolayer cells, Oil-Red-O-stained; D) adipocyte differentiation after 28 days is evidenced by formation of lipid filled droplet in the cytoplasm; Oil-Red-O-staining of lipid filled droplets in differentiated adipocytes; (one representative experiment is shown, n=6); Osteoblast differentiation. [F-G] Dedifferentiated chondrocytes were treated with osteogenic medium for 28 days. Successful differentiation was evaluated by von Kossa staining. E) stained negative control; F) accumulation of calcified matrix is demonstrated by von Kossa staining; (one representative experiment is shown, n=6); bar=50 µm.

In a first aspect, the present invention is directed to a three dimensional (3D) in vitro model which takes into consideration the close interaction and cooperation of cartilage and bone tissue. The present invention provides a 3D in vitro bi-phasic cartilage-bone organoid comprising:
  a) a layer of artificial cartilage tissue; and
  b) a layer of artificial bone tissue, wherein the artificial bone tissue comprises a structure-giving scaffold and a bone marrow structure;
    wherein the layer of artificial cartilage tissue contacts at least one surface of the layer of artificial bone tissue.

The artificial cartilage tissue 3D in vitro bi-phasic cartilage-bone organoid of can be prepared using mesenchymal progenitor cells, for example, using mesenchymal progenitor cells comprising at least 50% of or consist of cells that are CD105+, CD106+, CD44+, CD73+, CD90+ and CD13+, for example, from isolated primary chondrocytes. The artificial cartilage tissue may, for example, be prepared by a method of the present invention specified below.

The bone marrow structure of the artificial bone tissue of the 3D in vitro bi-phasic cartilage-bone organoid of the present invention is prepared by seeding mesenchymal stem cells on the structure-giving scaffold. The bone marrow structure of the artificial bone tissue can, for example, be prepared by seeding mesenchymal stem cells on the structure-giving scaffold and by adding hematopoietic stem cells after culturing of mesenchymal stem cell on the structure-giving scaffold for 2 to 10 days, for example, for 5 to 8 days, for example, for 7 days.

The structure-giving scaffold of the artificial bone tissue of the 3D in vitro bi-phasic cartilage-bone organoid of the present invention can, for example, comprise or consists of a biological or non-biological material, for example, of a 3D ceramic scaffold.

According to another aspect, the present invention is directed to a method of producing the 3D in vitro biphasic cartilage-bone organoid of the present invention. The method comprises or consists of the steps:
  seeding mesenchymal stem cells on a structure-giving scaffold;
  culturing the mesenchymal stem cells for 2 to 10 days on the structure-giving scaffold, for example, for 5 to 8 days, for example, for 7 days;
  adding hematopoietic stem cells to the mesenchymal stem cells cultured on the structure giving scaffold and culturing the resulting mixture for at least 5 days, for example, for 5 days to 8 weeks, for example, for 1 week to 4 weeks, in order to prepare a layer of artificial bone tissue comprising a structure-giving scaffold seeded with a bone marrow structure;
  providing artificial cartilage tissue prepared by a method of one of claims 13 to 15 and
  placing a layer of the artificial cartilage tissue on at least one surface of the layer of artificial bone tissue.

According to another aspect, the present invention is directed to a transplant comprising a 3D in vitro bi-phasic cartilage-bone organoid of the present invention.

Further, the present invention provides a pharmaceutical composition comprising a 3D in vitro bi-phasic cartilage-bone organoid of the present invention or a transplant of the present invention and at least one pharmaceutically acceptable excipient.

The present invention is also directed to a method for screening substances in vitro, which modulate properties of cartilage or bone tissue, comprising the steps of:
  providing a sample of a 3D in vitro bi-phasic cartilage-bone organoid of the present invention;
  dividing the respective sample into portions;
  incubating at least one portion with a substance to be screened; and
  comparing parameters measured for the treated portion with another portion that was not incubated with the substance to be screened.

According to a further aspect of the present invention, a self-contained 3D in vitro bi-phasic cartilage-bone organoid-on-a-chip device is provided, comprising at least one medium feed reservoir, at least one organ growth section comprising at least one organ cavity housing a 3D in vitro bi-phasic cartilage-bone organoid of the present invention, wherein the medium feed reservoir is connected to the at least one organ growth section by a microfluidic feed channel.

The present invention is also directed to a method of preparing chondrogenic cell aggregates, comprising the steps:

a) providing mesenchymal progenitor cells; and
  b) culturing the mesenchymal progenitor cells under non-adherent conditions to form chondrogenic cell aggregates.

The mesenchymal progenitor cells used in this method can, for example, comprise at least 50% of or consist of cells that are $CD105^+$, $CD106^+$, $CD44^+$, $CD73^+$, $CD90^+$ and $CD13^+$. The mesenchymal progenitor cells can, for example, comprise or consist of isolated primary chondrocytes.

The present invention is based on the finding that development and homeostasis of either bone tissue or cartilage tissue is influenced by the presence and interaction of both tissues. It has long been known that formation and differentiation of bone tissue is influenced by the presence, extend and direction of physical forces applied to the developing bone. In the natural environment these forces are often applied to bone tissue via its contact surface to cartilage tissue. One function of cartilage tissue is to properly transfer impact forces which originate from body movement to the underlying bone tissue. This interaction has not only an influence on the orientation and strength of bone tissue but also impacts the definition and organization of bone marrow and stem cell niches within the bone. It is beyond doubt that organization and differentiation of bone marrow and stem cell niches has a significant impact on the immune system of an individual. Both tissues, bone tissue and cartilage tissue, should thus be regarded as forming one common organ. The 3D in vitro bi-phasic cartilage-bone organoid of the present invention reflects this situation and allows mimicking the influence which the presence of both tissues has on the development and differentiation of bone tissue, respectively on organization and differentiation of bone marrow and stem cell niches, and cartilage tissue. Therefore, the 3D in vitro bi-phasic cartilage-bone organoid of the present invention allows for the first time studying the effect of the close interaction of both tissue types on each other. In particular if the 3D in vitro bi-phasic cartilage-bone organoid is used in a test system wherein the layer of artificial cartilage tissue can be exposed to defined physical forces by mechanical stimulation, a model system is provided which closely mimics the natural situation and, thus, allows for novel insight into the biology of these tissues as well as for a suitable screening system for substances which interact with these tissues or processes.

In the following, different aspects of the present invention are provided in more detail. Each aspect so defined may be combined with any other aspect or aspects unless clearly stated to the contrary. In particular, any feature indicated as being preferred, "for example" or advantageous may be combined with any other feature or features indicated as being part of the present invention or being indicated as being preferred, "for example" or advantageous.

The present invention is directed to a 3D in vitro bi-phasic cartilage-bone organoid. For the purpose of the present invention, the term "organoid" denotes an artificial, de novo generated, functional cell aggregate of different types of cells in vitro that shows at least one function which is typical for the respective organ or tissue, for example, that shows the majority of functions which are typical for the respective organ or tissue.

The 3D in vitro bi-phasic cartilage-bone organoid of the present invention comprises a layer of artificial cartilage tissue. An artificial cartilage tissue is a cartilage tissue that has been prepared and assembled de novo and in vitro. Usually artificial cartilage tissue comprises fully or at least partially differentiated chondrocytes and extracellular matrix components including collagen II, IX and XI.

There are numerous techniques available to the skilled person to prepare artificial cartilage tissue in vitro. Since cartilage tissue usually comprises more than a simple 2D layer of chondrocytes, artificial cartilage tissue generated from 3D culture techniques are preferred. Suitable techniques are summarized in Tortelli and Cancedda ("Three-dimensional cultures of osteogenic and chondrogenic cells: A tissue engineering approach to mimic bone and cartilage in vitro", European Cells and Materials (2009), 17, 1-14). The layer of artificial cartilage tissue can e.g., be derived from techniques comprising culturing and/or organisation of cells or cell aggregates by hydrogel encapsulation, micromass culture, formation of high density cell pellets, and use of biocompatible degradable or non-degradable scaffolds. Another method of preparing artificial cartilage tissue in the sense of the present invention is described further below as a method for preparing chondrogenic cell aggregates.

In order to provide a layer of artificial cartilage tissue, the artificial cartilage tissue is prepared using mesenchymal stem cells (MCS), also called mesenchymal progenitor cells. Isolated mesenchymal progenitor cells can, for example, be used. The term "isolated" means that the mesenchymal progenitor cells are cells that have been isolated from a natural source or represent progeny thereof which e.g., has been derived by cell proliferation. The mesenchymal progenitor cells used can, for example, be derived from cartilage tissue of a donor, individual or patient. The mesenchymal progenitor cells can, for example, be primary cells which have not been transformed or immortalized. In particular, the mesenchymal progenitor cells may comprise or consist of adult mesenchymal progenitor cells. Such adult mesenchymal progenitor cells are derived from non-embryonic cartilage tissue of a donor, individual or patient. The mesenchymal progenitor cells can be derived from cartilage tissue of any donor tissue that has been differentiated to comprise cartilage tissue. The mesenchymal progenitor cells can, for example, be derived from cartilage tissue of a joint, for example, from cartilage of a knee or elbow of a donor. The mesenchymal progenitor cells can, for example, be human cells. Human mesenchymal progenitor cells are derived from cartilage tissue of human origin. The mesenchymal progenitor cells may comprise at least 50% of cells that are $CD105^+$, $CD106^+$, $CD44^+$, $CD73^+$, $CD90^+$ and $CD13^+$ or may consist of cells that are $CD105^+$, $CD106^+$, $CD44^+$, $CD73^+$, $CD90^+$ and $CD13^+$. The mesenchymal progenitor cells can, for example, comprise or consist of isolated primary chondrocytes like e.g., human primary chondrocytes.

The 3D in vitro bi-phasic cartilage-bone organoid of the present invention comprises a layer of artificial bone tissue, wherein the artificial bone tissue comprises a structure-giving scaffold and a bone marrow structure. An artificial bone tissue is a bone tissue that has been prepared and assembled de novo and in vitro. Usually artificial bone tissue comprises fully or partially differentiated osteoblasts, osteoclasts and hematopoietic stem cells.

There are numerous techniques available to the skilled person to prepare artificial bone tissue in vitro. Since bone tissue usually comprises more than a simple 2D layer of a certain cell type, artificial bone tissue generated from 3D culture techniques are preferred. Suitable techniques are summarized in Tortelli and Cancedda ("Three-dimensional cultures of osteogenic and chondrogenic cells: A tissue engineering approach to mimic bone and cartilage in vitro", European Cells and Materials (2009), 17, 1-14). The layer of artificial bone tissue can e.g., be derived from techniques comprising culturing and/or organisation of cells or cell aggregates by micromass culture, and use of biocompatible degradable or non-degradable scaffolds. Suitable culture techniques and scaffolds are known in the art. E.g. biodegradable or non-degradable scaffolds comprising or consisting of a biological or non-biological material may be used. The use of synthetic based polymers as scaffold has been described as well as use of collagen-based scaffolds, metal-based scaffolds like e.g., titanium based scaffolds, or ceramic-based scaffolds.

The cells used for preparation of the artificial bone tissue may comprise mesenchymal stem cells (MSC) and hematopoietic stem cells (HSC). Isolated MSCs and/or isolated HSCs can, for example, be used. The term "isolated" means that MSCs and/or HSCs are cells that have been isolated from a natural source or represent progeny thereof which e.g., has been derived by cell proliferation. The MSCs and/or HSCs used can, for example, be derived from suitable tissue of a donor, individual or patient. The MSCs and/or HSCs can, for example, be primary cells which have not been transformed or immortalized. In particular, the MSCs and/or HSCs may comprise or consist of adult MSCs and/or HSCs. Such adult MSCs and/or HSCs are derived from non-embryonic tissue, for example, from bone or bone marrow tissue of a donor, individual or patient. The MSCs and/or HSCs can, for example, be human cells. Human MSCs and/or HSCs can, for example, be derived from bone or bone marrow tissue of human origin.

A method of preparing artificial bone tissue in the sense of the present invention comprises seeding and culturing MSCs on a ceramic 3D scaffold. The populated ceramic 3D scaffold is cultured for a predetermined period of time and subsequently HSCs may be added. In an embodiment, the HSCs can, for example, be added after culturing the MSCs on the ceramic scaffold for 2 to 10 days. The populated ceramic 3D scaffold is then further cultured either under static culture conditions or in a perfused system for continuous nutrient supply.

The techniques for generating artificial bone tissue can be further amended. For example growth factors or other signalling molecules can be added to support bone marrow functions. Hypoxic conditions may be used that are similar to the natural conditions bone marrow has to face. The culture times may have to be optimized as well as the sequence of administration of the various cell types to the scaffold. In addition to MSCs and HSCs further cell types may be used for generation of artificial bone tissue. These additional cells may comprise cell types which normally occur in bone or bone marrow structures e.g., immune cells, endothelial cells and the like.

The 3D in vitro bi-phasic cartilage-bone organoid of the present invention may be used as a research tool in vitro and/or in vivo. It may be used to investigate the biology or one or more of its components. Alternatively it may be used in a method of screening for substances in vitro and/or in vivo, which modulate properties of cartilage or bone tissue.

The present invention is also directed to a transplant comprising a 3D in vitro bi-phasic cartilage-bone organoid of the present invention and to a pharmaceutical composition comprising a 3D in vitro bi-phasic cartilage-bone organoid of the present invention or a transplant of the present invention and at least one pharmaceutically acceptable excipient.

In a further aspect, the present invention is directed to a method for screening substances in vitro, which modulate properties of cartilage or bone tissue, comprising the steps of:

providing a sample of a 3D in vitro bi-phasic cartilage-bone organoid of the present invention;
dividing the respective sample into portions;
incubating at least one portion with a substance to be screened; and
comparing parameters measured for the treated portion with another portion that was not incubated with the substance to be screened.

In an embodiment, the portion can, for example, be subjected to a self-contained organ-on-a-chip device prior to incubating the portion with a substance to be screened.

Briefly, the inventive method makes the identification and analysis of substances possible, which exert an influence on cartilage or bone tissue via the 3D in vitro bi-phasic cartilage-bone organoid of the present invention. The sample, which shall be understood to comprise a certain number of product subjects according to the present invention, is divided into multiple portions. At least two subsets are provided; one is used for screening while the other one serves as negative control. The number of screening parts can, for example, exceed the number of control parts. Usually, numerous portions are subjected to a high-throughput screening. The substances to be screened in the inventive method are not restricted anyway. In an embodiment of the present invention, the substances are selected from the group of nucleic acids including RNAi, ribozymes, aptamers, antibodies, peptides, carbohydrates, polymers, small molecules having a molecular weight between 50 and 1.000 Da, and proteins, for example, antibodies, cytokines and lipocalins. These substances are often available in libraries. A single compound can, for example, be incubated within a distinct portion of the sample. It is also possible, however, to investigate the cooperative effect of substances by incubating at least two substances within one portion. A further subset of subjects is simultaneously incubated in the absence of the substances. The incubation process depends on various parameters, e.g., the cell types and the sensitivity of detection, which optimization follows routine procedures known to those skilled in the art. The identification of effective substances in the meaning of the present invention can, for example, be indirectly performed, e.g., by determining the expression patterns and/or the cell viability, which are altered. The determination may be performed at a specified moment and correlated to the signal strength at the beginning of the experiment and the negative control. Suitable tests are known to those skilled in the art or can be easily designed as a matter of routine.

The present invention also discloses a self-contained 3D in vitro bi-phasic cartilage-bone organoid-on-a-chip device comprising a self-contained organ-on-a-chip device as described in WO 2009/146911 and a 3D in vitro bi-phasic cartilage-bone organoid of the present invention.

The self-contained 3D in vitro bi-phasic cartilage-bone organoid-on-a-chip device of the present invention is formed to allow establishing or maintaining the 3D in vitro bi-phasic cartilage-bone organoid of the present invention in a miniaturized chip format, suitable for online observation by live cell imaging and for example two photon microscopy and their use for, e.g., testing the activity, pharmacodynamic and pharmacokinetic of compounds or to study self-assembly, homeostasis, damage, regeneration or interaction of organs or organoids and stem cell niches, as well as phenomena of maturation, aging, death and chronobiology. For that purpose, the self-contained 3D in vitro bi-phasic cartilage-bone organoid-on-a-chip device of the present invention comprises at least one medium feed reservoir, at least one organ growth section comprising at least one organ cavity housing a 3D in vitro bi-phasic cartilage-bone organoid of the present invention, wherein the medium feed reservoir is connected to the at least one organ growth section by a microfluidic feed channel.

Subject matter of the present invention allows the establishment of miniaturized in vitro culture of an organoid comprising cartilage and bone tissue. The resulting 3D in vitro bi-phasic cartilage-bone organoid of the present invention is suitable for long term culture of up to 3 months when cultured e.g., under conditions allowing for continuous supply with oxygen and nutrients like e.g., continuous perfusion conditions.

Subject matter of the present invention allows the integration of mechanical stimuli to mimic e.g., physical forces originating from body movement and the induction of vascular structures within the organoid and, thus, the provision of an environment that comes close to the natural situation. Based on these properties, subject matter of the present invention allows for generation of various scientific findings in the field of tissue engineering, molecular biology of cell and tissue differentiation as well as regenerative medicine. Subject matter of the present invention may also lead to replacement of cost and labor intensive animal experiments by in vitro tests.

At present there has been no attempt to provide a 3D in vitro organoid which combines the functionally interrelated tissues bone, bone marrow and cartilage in one single integrated system, which is compatible with prolonged culture techniques like perfusion culture and which allows the induction of vascularisation. By exposure of the system to mechanical forces or other stimuli, the natural environment will be mimicked to an extent that has never been reached before.

In another aspect, the present invention is directed to a method of preparing in vitro a chondrogenic cell aggregate. The method comprises the steps of:
a) providing isolated mesenchymal progenitor cells; and
b) culturing the mesenchymal progenitor cells under non-adherent conditions to form a chondrogenic cell aggregate.

It has surprisingly been found that isolated mesenchymal progenitor cells are capable of forming a three dimensional cell aggregate which exhibits chondrogenic differentiation without influence of embryonic cells. This effect is achieved by culturing the mesenchymal progenitor cells under non-adherent conditions. It could be shown that under such non-adherent culture conditions the mesenchymal progenitor cells arrange freely to each other and condense to a cell aggregate which exhibits expression of markers specific for chondrogenic differentiation and which is therefore denoted chondrogenic cell aggregate.

In the following, different aspects of the present invention are provided in more detail. Each aspect so defined may be combined with any other aspect or aspects unless clearly stated to the contrary. In particular, any feature indicated as being preferred, "for example" or advantageous may be combined with any other feature or features indicated as being part of the present invention or being indicated as being preferred, "for example" or advantageous.

The method of the present invention is directed to the preparation of a chondrogenic cell aggregate in vitro. For the purpose of the present invention the term "chondrogenic cell aggregate" refers to a functional cell aggregate that exhibits at least one function that is specific for chondrocytes or cartilage tissue. The chondrogenic cell aggregate of the present invention can, for example, exhibit the majority or essentially all organ or tissue functions of differentiated chondrocytes or cartilage tissue. In particular the chondrogenic cell aggregate of the present invention may behave like a functional cartilage tissue and/or is capable of inducing cartilage development or differentiation in vitro and/or in vivo. The chondrogenic cell aggregate of the present invention may be characterized by elevated expression of marker genes or proteins that are associated with development or differentiation of chondrocytes or cartilage tissue. The chondrogenic cell aggregate of the present invention may be characterized by up regulated expression of collagen II, IX and XI as well as down regulated expression of collagen I and XII compared to expression in the mesenchymal progenitor cells immediately prior to subjecting to non-adherent culturing conditions.

The chondrogenic cell aggregate of the present invention is formed by a method of the present invention. The chondrogenic cell aggregate may exhibit a cell aggregate with a substantially rounded or spherical shape. It may have an average diameter of 0.5 mm to 3 mm, for example, with an average diameter of 0.5 mm to 2 mm. The chondrogenic cell aggregate of the present invention is free of any artificial biological or non-biological scaffold or carrier which does not originate from the cells used in the production of chondrogenic cell aggregate. The chondrogenic cell aggregate of the present invention can, for example, consist of the cell aggregate formed by a method of the present invention, wherein the method has been conducted without the use or addition of any biological or non-biological scaffold or carrier which does not directly originate from the cells used in the method.

In the method of the present invention, isolated mesenchymal progenitor cells are used. The term "isolated" means that the mesenchymal progenitor cells are cells that have been isolated from a natural source or progeny thereof which e.g., has been derived by cell proliferation. The mesenchymal progenitor cells used can, for example, be derived from cartilage tissue of a donor, subject or patient. The mesenchymal progenitor cells can, for example, be primary cells which have not been transformed or immortalized. In particular, the mesenchymal progenitor cells may comprise or consist of adult mesenchymal progenitor cells. Such adult mesenchymal progenitor cells are derived from non-embryonic cartilage tissue of a donor, subject or patient. The mesenchymal progenitor cells can be derived from cartilage tissue of any donor tissue that has been differentiated to comprise cartilage tissue. The mesenchymal progenitor cells can, for example, be derived from cartilage tissue of a joint, for example, from cartilage of a knee or elbow of a donor. The mesenchymal progenitor cells used in the method of the present invention can, for example, be human cells. Human mesenchymal progenitor cells are derived from cartilage tissue of human origin. The mesenchymal progenitor cells may comprise at least 50% of cells that are $CD105^+$, $CD106^+$, $CD44^+$, $CD73^+$, $CD90^+$ and $CD13^+$ or may consist of cells that are $CD105^+$, $CD106^+$, $CD44^+$, $CD73^+$, $CD90^+$ and $CD13^+$. The mesenchymal progenitor cells can, for example, comprise or consist of isolated primary chondrocytes like e.g., human primary chondrocytes.

In the method of the present invention, the mesenchymal progenitor cells can be subjected to culturing under non-adherent conditions at any stage after isolation. The formation of cell aggregates is further enhanced, however, if the mesenchymal progenitor cells have undergone at least some culturing under adherent 2D monolayer conditions. The mesenchymal progenitor cells can, for example, have been cultured in 2D monolayer culture for at least 5 passages prior to subjecting to culturing under non-adherent conditions. In order to provide a dedifferentiated phenotype, it is desirable to culture the mesenchymal progenitor cells in 2D monolayer adherent conditions for at least 10 passages. A high efficiency in formation of cell aggregates is maintained over a broad spectrum of passages. It has been found, however, that best results are achieved if the mesenchymal progenitor cells have been cultured in 2D monolayer culture for at least 5 passages and not more than 20 passages. The mesenchymal progenitor cells can, for example, be subjected to non-adherent culture after culture in 2D monolayer for at least 5 passages and not more than 15 passages after isolation.

In the method of the present invention, after provision of the isolated mesenchymal progenitor cells, the mesenchymal progenitor cells are subjected to non-adherent culture conditions to form chondrogenic cell aggregates.

The formation of cell aggregates is particularly effective if the mesenchymal progenitor cells are subjected to non-adherent culture conditions at a certain concentration. If the concentration is too low, cells have only rarely contact to each other and condensation to cell aggregates is less effective. On the other hand, if the concentration of mesenchymal progenitor cells is too high, cells are less flexible or mobile and, thus, the formation of cell aggregates is less effective. The mesenchymal progenitor cells can, for example, be subjected to non-adherent culture conditions at a concentration of $5 \times 10^4$ to $5 \times 10^7$ per ml. Even better results are achieved if the mesenchymal progenitor cells are subjected to non-adherent culture conditions at a concentration of $1 \times 10^5$ to $1 \times 10^7$ per ml, for example, of $5 \times 10^5$ to $5 \times 10^6$ per ml, and, for example, of $9 \times 10^5$ to $1.1 \times 10^6$ per ml.

In the method of the present invention, the isolated mesenchymal progenitor cells are cultured under non-adherent culture conditions. This means that mesenchymal progenitor cells are cultured under conditions wherein the cells do not adopt a flattened, spread-out shape indicating strong attachment and adherence to the culture surface. The mesenchymal progenitor cells after seeding can, for example, remain rounded and, if at all, only weakly associated with the culture surface. Appropriate means for non-adherent cell culture are well known in the art. Non-adherent culture conditions may comprise culture of the mesenchymal progenitor cells in culture vessels with a culture surface that does not support adherence of the mesenchymal progenitor cells. E.g., culture vessels with culture surfaces exhibiting ultra-low cell attachment can be used. For that purpose culture vessels with a neutral or positively charged culture surface may be used. The culture surface may be coated by a layer of a material which further reduces interaction of the mesenchymal progenitor cells and the culture surface. The culture surface may be covered with a hydrophilic hydrogel.

It appears that under non-adherent culture conditions, the mesenchymal progenitor cells associate and condense to cell aggregates rather quickly. Already after 24 hours of non-adherent cell culture, the mesenchymal progenitor cells aggregated into one large complex. In order to prepare cell aggregates that represent chondrogenic cell aggregates with progressed development, differentiation and/or function, it is beneficial, however, to conduct non-adherent culturing for a period of time that exceeds 24 hours. In the method of the present invention, the mesenchymal progenitor cells may be cultured under non-adherent conditions for at least 48 hours, for example, for at least 72 hours, for example, for at least 1 week, for example, for at least 2 weeks, for example, for at least 4 weeks. The mesenchymal progenitor cells may thus be cultured under non-adherent conditions for 48 hours to 8 weeks, for example, for 60 hours to 6 weeks, for example, for 72 hours to 5 weeks. Upon cultivation in normal culture dishes, aggregates adhere to the dish surfaces and the cells start to migrate and proliferate resulting in disintegration of the aggregate structure. The aggregates can, for example, therefore kept under non adhered conditions for the entire period of cultivation.

In the method of the present invention, the mesenchymal progenitor cells can, for example, be cultured under non-adherent conditions at least until a cell aggregate is formed which exhibits a rounded shape with an average diameter of 0.5 mm to 3 mm, for example, with an average diameter of 0.5 mm to 2 mm.

The suitability of the chondrogenic cell aggregate generated by the method of the present invention is dependent on its ability to induce or provide differentiated chondrocytes or cartilage tissue. The isolated mesenchymal progenitor cells can, for example, be cultured under non-adherent conditions until the resulting cell aggregate starts to exhibit properties and/or functions of partially or fully differentiated chondrocytes or cartilage tissue. The progression in differentiation can be monitored by the relative expression of respective marker genes, proteins or structures. The isolated mesenchymal progenitor cells can, for example, be cultured under non-adherent conditions at least until the cell aggregate formed exhibits up regulated expression of collagen II, IX and XI as well as down regulated expression of collagen I and XII compared to expression in the mesenchymal progenitor cells immediately prior to subjecting to non-adherent culturing conditions. Since expression analysis for stage specific marker molecules revealed maintained expression of N-Cadherin and elevated levels of Collagen type II but no expression of Collagen type X, a differentiated phenotype between chondrogenic precursor and columnar chondrocyte, but no further differentiation to the prehypertrophic stage is suggested. This phenotype reflects the arrested phenotype of chondrocytes in articular cartilage tissues. Relative expression levels of genes can easily be determined by well known methods like e.g., quantitative or semi-quantitative RT-PCR or Northern blotting. Relative expression levels of proteins can also be determined by well known methods like e.g., Western blotting and ELISA techniques. In addition to the analysis of the expression pattern on mRNA and protein level further detailed characterization of the aggregate structure by immune histochemical staining as well as pressure resistance determination will be included to assign the quality of the aggregate.

One of the drawbacks encountered with most of the methods of the prior art is that in these methods, the presence of an artificial biological or non-biological scaffold or carrier is needed on or within which cells are cultured to form cartilage tissue. A biological or non-biological scaffold or carrier is regarded as artificial or added if the scaffold or carrier is provided from the outside and is not directly formed by the cells used in the method of the present invention during formation of cell aggregates. In the method of the present invention, the use or presence of such an artificial biological or non-biological scaffold or carrier is not needed. The method of the present invention yields an chondrogenic cell aggregate according to the present invention without the use of any such artificial biological or non-biological scaffold or carrier which does not originate from the cells used. In an embodiment, the method of the present invention can, for example, be performed such that no addition of biological or non-biological scaffold is performed in the formation of chondrogenic cell aggregates.

In the method of the present invention, the mesenchymal progenitor cells are cultured in adherent or non-adherent conditions with standard medium. There is no specialized culture medium necessary to induce proper cell aggregation under non-adherent conditions. The skilled person is well aware of suitable media. Typically standard DMEM is used with a certain content of fetal calf serum (FCS), for example, FCS is present in a concentration of 5% to 15%, for example, in a concentration of 10% FCS.

Despite the fact, that proper chondrogenic differentiation is induced upon aggregate formation without additional treatments, a further optimization may be beneficial. Therefore, in the method of the present invention once the aggregation process is completed further optimization steps regarding growth factor administration or cultivation under hypoxic conditions will further improve development and differentiation.

The present invention is also directed to a transplant comprising or consisting of an artificial chondrogenic cell aggregate of the present invention or of a tissue or structure derived therefrom.

In another aspect of the present invention a pharmaceutical composition is provided comprising an artificial chondrogenic cell aggregate of the present invention, a tissue or structure derived therefrom or a transplant of the present invention and at least one pharmaceutically acceptable excipient.

The artificial chondrogenic cell aggregate of the present invention, the transplant of the present invention or the pharmaceutical composition of the present invention may be used in the treatment of cartilage impairment and/or destruction or loss of cartilage.

Since the method of the present invention works with isolated mesenchymal progenitor cells derived from non-embryonic sources, the method allows the production of artificial chondrogenic cell aggregate starting from cells derived from a particular donor or patient. It is thus possible to provide artificial chondrogenic cell aggregates that have been derived from the cells of the person to be treated with the artificial chondrogenic cell aggregates, pharmaceutical composition or transplant of the present invention. It thus appears possible to provide a transplant that is mainly, substantially or completely derived from cells of the recipient of the transplant himself so that rejection reactions will be reduced to a minimum or will be completely absent.

The artificial chondrogenic cell aggregate of the present invention may be used for the in vitro or in vivo generation of differentiated chondrocytes or cartilage tissue.

The artificial chondrogenic cell aggregate of the present invention, the transplant of the present invention or the pharmaceutical composition of the present invention may be used as a research tool that can be used in vitro and in vivo.

The artificial chondrogenic cell aggregate of the present invention, the transplant of the present invention or the pharmaceutical composition of the present invention may be used in a method of screening for substances in vitro or in vivo, which modulate properties of chondrocytes or cartilage tissue.

The present invention additionally teaches a method for screening substances in vitro, which modulate properties of chondrocytes or cartilage tissue, comprising the steps of:
    providing a sample of an artificial chondrogenic cell aggregate of the present invention or a cell aggregate prepared by a method of the present invention or a tissue derived therefrom;
    dividing the respective sample into portions;

incubating at least one portion with a substance to be screened; and comparing parameters measured for the treated portion with another portion that was not incubated with the substance to be screened.

In an embodiment, the portion can, for example, be subjected to a self-contained organ-on-a chip device prior to incubating the portion with a substance to be screened.

Briefly, the inventive method makes the identification and analysis of substances possible, which exert an influence on chondrocytes or cartilage tissue via the artificial chondrogenic cell aggregate of the present invention. The sample, which shall be understood to comprise a certain number of product subjects according to the present invention, is divided into multiple portions. At least two subsets are provided; one is used for screening while the other one serves as negative control. The number of screening parts can, for example, exceed the number of control parts. Usually, numerous portions are subjected to a high-throughput screening. The substances to be screened in the inventive method are not restricted anyway. In an embodiment of the present invention, the substances are selected from the group of nucleic acids including RNAi, ribozymes, aptamers, antibodies, peptides, carbohydrates, polymers, small molecules having a molecular weight between 50 and 1.000 Da, and proteins, for example, antibodies, cytokines and lipocalins. These substances are often available in libraries. A single compound can, for example, be incubated within a distinct portion of the sample. It is also possible, however, to investigate the cooperative effect of substances by incubating at least two substances within one portion. A further subset of subjects is simultaneously incubated in the absence of the substances. The incubation process depends on various parameters, e.g., the cell types and the sensitivity of detection, which optimization follows routine procedures known to those skilled in the art. The identification of effective substances in the meaning of the present invention can, for example, be indirectly performed, e.g., by determining the expression patterns and/or the cell viability, which are altered. The determination may be performed at a specified moment and correlated to the signal strength at the beginning of the experiment and the negative control. Suitable tests are known to those skilled in the art or can be easily designed as a matter of routine.

Since the artificial chondrogenic cell aggregate of the present invention can be regarded as an organ, organoid or a precursor of an organ or part thereof, it may be particularly beneficial to use a test system wherein the artificial chondrogenic cell aggregate can be prepared and/or cultured for a prolonged time under conditions which mimic natural perfusion. It appears particularly suitable to combine the method of the present invention and/or the artificial chondrogenic cell aggregate of the present invention in an assay system based on the self-contained organ-on-a-chip device system described in the European patent application with the filing number EP 10 008 244 or in the PCT application with the publication number WO2009/146911.

The present invention also discloses a self-contained artificial chondrogenic cell aggregate organoid-on-a-chip device comprising a self-contained organ-on-a-chip device as described in WO 2009/146911 and an artificial chondrogenic cell aggregate of the present invention.

The self-contained artificial chondrogenic cell aggregate organoid-on-a-chip device of the present invention is formed to allow establishing or maintaining the artificial chondrogenic cell aggregate of the present invention in a miniaturized chip format, suitable for online observation by live cell imaging and for example two photon microscopy and their use for, e.g., testing the activity, pharmacodynamic and pharmacokinetic of compounds or to study self-assembly, homeostasis, damage, regeneration or interaction of organs or organoids and stem cell niches, as well as phenomena of maturation, aging, death and chronobiology. For that purpose, the self-contained artificial chondrogenic cell aggregate organoid-on-a-chip device of the present invention comprises at least one medium feed reservoir, at least one organ growth section comprising at least one organ cavity housing an artificial chondrogenic cell aggregate of the present invention, wherein the medium feed reservoir is connected to the at least one organ growth section by a microfluidic feed channel.

The present invention provides for the first time an artificial chondrogenic cell aggregate and a method of producing the same, which is characterized by non-forced cell assembly, the lack of requirement of any artificial biological or non-biological scaffold or carrier and which is produced from adult cells so that no embryonic cells or tissues are needed.

The artificial chondrogenic cell aggregate of the present invention represents a functional inductive aggregate which is capable of inducing or initiating cartilage tissue development in vitro and in vivo. The resulting cartilage tissue is characterized by the verifiable presence of structures typically forming part of cartilage tissue which are arranged in the physiological order.

EXAMPLES

Example A

I. Formation of Artificial Bone Tissue
Cells

Mesenchymal stem cells (MSC) are isolated by standard procedures. Briefly, bone marrow aspirates were intensively rinsed with PBS and PBMC (peripheral blood mononuclear cells) were isolated by Ficoll density gradient centrifugation. Mesenchymal progenitors are isolated by plastic adherence followed by an amplification period up to 4 passages. Human hematopoietic stem cells were isolated from umbilical blood samples by CD34 expression using the MACS technology (Miltenyi Biotec). HSC were cultivated in supplemented media (Stemspan®+100 ng/ml of TPO,FLT3, IL6 and SCF).
Platform The platform for the artificial bone marrow is provided by a 3D ceramic scaffold (Sponceram® Zellwerk). In order to induce coordinated proliferation, differentiation and readjustment of the microenvironment according to extracellular matrix deposition and signalling molecule expression mesenchymal stem cells are seeded on this ceramics one week prior the addition of hematopoietic stem cells. The ceramic is than further cultivated either in static culture or in a perfused system for continuously nutrient supply. Functionality of the bone marrow is evaluated by gene expression analysis, composition of different cell population by FACS technology and determination of typical biological functions (HSC maintenance and proliferation, development of individual stem cell niches, immunological issues).

II. Formation of Chondrogenic Cell Aggregates or Artificial Cartilage Tissue

Osteoarthritis and rheumatoid arthritis are degenerative diseases that both affect the cartilage structure. Initiated by various factors (e.g., mechanical overload, age, injury, and inflammation), the tissue structure gets irreversibly lost because the cells within the cartilage have only a very low intrinsic capacity for self-repair. Therefore, many efforts have been done within the last decades to find alternative strategies for the induction of a regeneration process of cartilage. In recent years the application of autologous cells in regenerative medicine is a subject of intense research. Both the ideal source of mesenchymal progenitor cells and optimal culture conditions for in vitro differentiation, however, remain to be established. Mesenchymal stromal/stem cells stand out due to their ability to differentiate in all mesenchymal tissues, though the number of cells that can be obtained from bone marrow or other tissue sources is restricted. Therefore, usage of autologous cells isolated from healthy tissue followed by amplification represents one promising strategy to solve this challenge.

Unfortunately, cells lose their differentiated phenotype upon withdrawal of their normal tissue microenvironment. Isolation of chondrocytes from their normal three dimensional articular cartilage matrix by enzymatic digestion and subsequent two dimensional monolayer cultivation thus leads to cellular alterations, a process during which the cells re-enter the cell cycle, lose their round phenotype and switch their matrix molecule production from Collagen types II, IX and XI to types I, III and V. Additionally, it has been demonstrated that 2D-cultivated chondrocytes express mesenchymal stem cell surface markers and possess multilineage differentiation potential. This process is referred to as dedifferentiation and underlines the importance of an intact 3D surrounding for the maintenance of the chondrocyte phenotype. Consequently, in recent years it emerged that developmental processes are not only controlled by soluble factors but in addition spatial arrangements provided by adhesive molecules, which not only mediate cell-cell and cell-matrix interaction but also contribute to gene expression regulation by adhesive signalling. Therefore, culturing progenitor cells in a 3D structure appears to be one of the key stimulatory factors during the process of chondrogenic redifferentiation in vitro. Hence, various 3D culture systems have been established for that purpose. Four techniques to culture mesenchymal or progenitor cells in a 3D system are commonly used: 1) hydrogel encapsulation, 2) micromass culture, 3) high density cell pellets and 4) biocompatible scaffolds.

Cultivation in a 3D microenvironment and prevention of monolayer formation is the principle of all mentioned culture systems. Despite the fact that all culture models are capable to induce chondrogenic differentiation proven by up regulation of Collagen type II and proteoglycan, significant deficiencies still remain. The cells are forced to form the cellular 3D aggregates either by centrifugation (pellet culture) or by gravity (micromass). On the other hand the ability for cellular interaction is limited or even impossible upon hydrogel encapsulation or cultivation on biocompatible scaffolds. It seems reasonable, however, to mimic the entire in vivo process of chondrocyte differentiation in vitro to obtain both the optimal prerequisite for regenerative applications and to provide a model culture system to expand the competent knowledge of this multistep process.

Mesenchymal condensation represents the initial step in the development of skeletal elements, where progenitors migrate to the site of future skeleton formation and start to accumulate and condensate resulting in high density cell aggregates. During the process of in vitro redifferentiation it is of primary interest to integrate this initial step of aggregate formation. Unfortunately, none of the common 3D culture systems is suitable for such a purpose since all lack the precondition of independent single cell mobility prior to the condensation process.

A scaffold free cultivation system was established comprising initial cellular condensation and subsequent chondrogenic redifferentiation of isolated dedifferentiated chondrocytes. The condensation process as well as the redifferentiated cells were intensively characterized by comprehensive gene expression analysis. Since the chondrogenic differentiation is demonstrated by strong up regulation of Collagen type II expression and massive secretion and accumulation of proteoglycans, this new 3D culture system provides for the first time the opportunity to investigate a mesenchymal condensation simulating process in vitro. Inhibition of chemokine signalling during cell aggregation demonstrated that the condensation process is independent of cell migration, but is rather mediated by adhesion molecules and intensified cell-cell contact.

Materials and Methods

Isolation and Culture of Primary Chondrocytes

Articular knee cartilage from voluntary donors was obtained from the Musculoskeletal Research Center Berlin, Charité (Universitätsmedizin Berlin, Germany) as well as from the Institute of Experimental Pathology Charité, Campus Virchow. The study was approved by the local ethics committee (Charité Campus Mitte, University Hospital Berlin). Cartilage tissue was minced into small pieces and chondrocytes were released by enzymatic digestion overnight at 37 C using Collagenase (1 mg/ml, Sigma-Aldrich) in DMEM. Cells were separated from the digested tissue by filtration through a 70 µm Nylon cell strainer (BD Falcon™, Belgium), washed with PBS and cultured in DMEM containing 10% FCS. Primary chondrocytes were cultivated in a water-jacked incubator with humidified atmosphere (5% $CO_2$/air) at 37° C. in DMEM medium (Gibco) supplemented with 10% FCS and penicillin/streptomycin (Gibco). The cells were passaged at least 10 times to yield in a complete dedifferentiated phenotype.

Characterization of Dedifferentiated Chondrocytes

Surface Expression Analysis by FACS

Dedifferentiated chondrocytes were analyzed for their expression of various mesenchymal stem cell (MSC) surface marker molecules by direct immunofluorescent staining. Cells were harvested by trypsinisation and centrifugation and the cell pellet was resuspended in PBS/BSA (0.5%). Cells were incubated with fluorescent-labelled antibodies for 15 min. at RT. As isotype controls cells were stained with T-cell marker molecules of the same isotype as the MSC antibodies. Staining assays were then washed with PBS/BSA and centrifuged to remove unbound antibodies. The cell pellets were resuspended in 400 µl PBS/BSA and analyzed on a FACSCalibur™ (BD Biosciences). For the detection of dead cells propidium jodid was added immediately before cytometric analysis. 30,000 events were acquired and analyzed using the CellQuest™ software.

Differentiation Potential

Adipogenic differentiation was induced in 2D cultures using well established medium supplements (DMEM with 10% FCS, 10 µg/ml Insulin, 0.2 mM Indomethacin, 1 µM Dexamethasone, 0.5 mM 3-isobutyl-1methyl-xanthine (Sigma)). Dedifferentiated chondrocytes were seeded in 6 well plates (Corning—100.000 cells per well) and cultured in DMEM+10% FCS until cells were confluent. The cells were stimulated for 28 days with medium replaced every 4 days. Oil-Red-O-staining for lipids After 28d of cells were fixed in 4% paraformaldehyd for 10 min, washed with PBS and subsequently incubated with freshly filtrated Oil Red O staining solution (0.7% in propylen glycerol) for 1 h (Sigma). After rinsing the cells two times with aqua dest. the staining was evaluated by light microscopy.

Osteogenic differentiation was induced in monolayer cultures with appropriate differentiation medium (DMEM+ 10% FCS, 10 mM β-glycerophosphate (Sigma), 10 nM Dexamethasone (Sigma), 0.1 mM Lascorbic acid 2-phosphate (Sigma). Briefly, cell were seeded in 6 well plates (Corning—100.000 cells per well) and cultured in DMEM+ 10% FCS until cells reached confluence. Medium was replaced every 4 days and after 21 days of osteogenic stimulation the cells were stained by von Kossa stain for secreted Ca2+ based mineralized matrix as marker for osteoblast differentiation. Cells were fixed with 4% Paraformaldehyd (Sigma). Silver nitrat solution (5%, Sigma) was given to the fixed cells and the culture plate was placed in UV light for 20 min. Finally the cells were rinsed with water and evaluation was done by light microscopy.

3D Culture Systems

For 3D low attachment culture, dedifferentiated chondrocytes were harvested and resuspended in DMEM+10% FCS to yield up in a single cell suspension of 106 cells per ml. The cell suspension (1 ml per well) was given to 24 well low attachment plate (Ultra Low Cluster Plate, Corning, Germany). In contrast to the negatively charged, hydrophilic surface of standard tissue culture dishes the ultra low attachment plates possess a neutral, hydrophilic hydrogel coated surface that greatly minimizes the binding of attachment proteins. By using this specialized culture dishes the cells do not settle down in an oligolayer construct through cell adhesion as in micromass culture. The formation of a 2D monolayer culture was prevented and the cells retained a round shape under this suspension culture maintaining conditions. Furthermore, in contrast to the pellet culture system, where the cells are forced to settle down by centrifugation, the low attachment culture system provides the opportunity for free cell movement and cell cell interaction during an initial condensation process. To provide constant culture conditions medium was changed regularly every 3 days. In order to interfere with chemotactical signalling elicited by G-Protein coupled receptors in the low attachment culture Pertussis Toxine (Sigma, Germany) was administered to culture medium in low attachment condensation experiments in different concentrations (10, 100 and 1000 ng/ml).

Histology

Sections of harvested aggregates were cut on a cryostat of 5-μm thickness and mounted on Superfrost Plus glass slides (Menzel). Slides were dried and fixed.

Heamatoxylin Staining

Sections were incubated in a heamatoxylin staining solution (Sigma) for 3 min and subsequently rinsed in tap water. Sections were dehydrated and mounted. Stained sections were analysed by light microscopy.

Alcian Blue Staining

Slides were preincubated in 3% acidic acid for 3 min before treatment with Alcian Blue (Sigma) (3% in 3% acetic acid) solution for 30 min at room temperature. Sections were washed with water, dehydrated and mounted. Stained sections were analysed by light microscopy.

Collagen Type II Stain

Slides were treated with a protein block (Dako Cytomation) for 10 min. at RT and then incubated overnight at 4 C with the primary monoclonal antibody against Collagen type 2A (BD Biosciences). The next day sections were incubated for 1 h with a Cy3-coupled secondary antibody (Dako Cytomation) and nuclei were counterstained by DAPI. Stained sections were analysed by fluorescence microscopy.

Real Time PCR

To the indicated points in time cells were lysed, RNA was extracted using the NucleoSpin® RNA II kit (Machery and Nagel). cDNA was synthesized by reverse transcription of 400 ng total RNA (Taqman, Roche). Real time PCR experiments were performed using the following conditions: 1 μl cDNA, 0.5 μM primer each, 6 mM MgCl2, 200 mM dNTP, 50 mM Tris (pH 8.8), 500 ng/ml BSA, Immolase 0.05 U/ml (Bioline), 1× Sybrgreen (Molecular Probes). The relative level of expression is given as ratio to GAPDH expression.

DNA Microarray Analysis

Human genome CGH Microarray 44K (Agilent) was utilized according to manufactures protocol. The microarray experiment was based on two-color ratio hybridization and a Low RNA Input Fluorescent Linear Amplification kit (Agilent) for RNA labeling. In brief, 500 ng of total RNA was reverse transcribed with an oligo(dT)-T7 promoter primer and Moloney murine leukaemia virus-reverse transcriptase (MMLV-RT) to synthesize first and second-strand of cDNA. Fluorescent anti-sense cRNA was synthesized with T7 RNA polymerase that simultaneously incorporates either cyanine 3-cytidine 5'-triphosphate (3-CTP) or cyanine 5-CTP. The purified products were quantified by absorbance at A552 nm for cyanine 3-CTP and A650 nm for cyanine 5-CTP, and labeling efficiency was verified with a Nanodrop photometer (Kisker). Before hybridization, 2 μg of each labeled cRNA product were fragmented and mixed with control targets and hybridization buffer according to the supplier's protocol (Agilent). Hybridizations were done overnight for at 60° C. Slides were then washed and scanning of microarrays was performed with 5-μm resolution using a DNA micro array laser scanner (Agilent). Features were extracted with an image analysis tool version A 6.1.1 (Agilent) using default settings. Data analysis was conducted on the Rosetta Informatics Platform Resolver Built 4.0. Changes in expression patterns were identified by stringent data evaluation and a 2-fold expression cut-off in combination with the requirements that only data points with a low p value (p<0.05) were selected. By use of this strategy, data evaluation was independent of error models implemented in the Rosetta Resolver system (Agilent).

Results

In order to accomplish a complete phenotypic dedifferentiation the isolated chondrocytes were cultured for at least ten passages in monolayer. As described previously, the cells adopted the definite progenitor phenotype marked by the expression of MSC surface markers (CD105, CD106, CD44, CD73, CD90 and CD13) and a multiple differentiation potential (adipocyte and osteocyte) (FIG. 1) (Rosowski et al., 2006). According to surface expression a uniform population of dedifferentiated chondrocytes was observed.

Cellular Condensation Upon Low Attachment Cultivation

Figure 2:
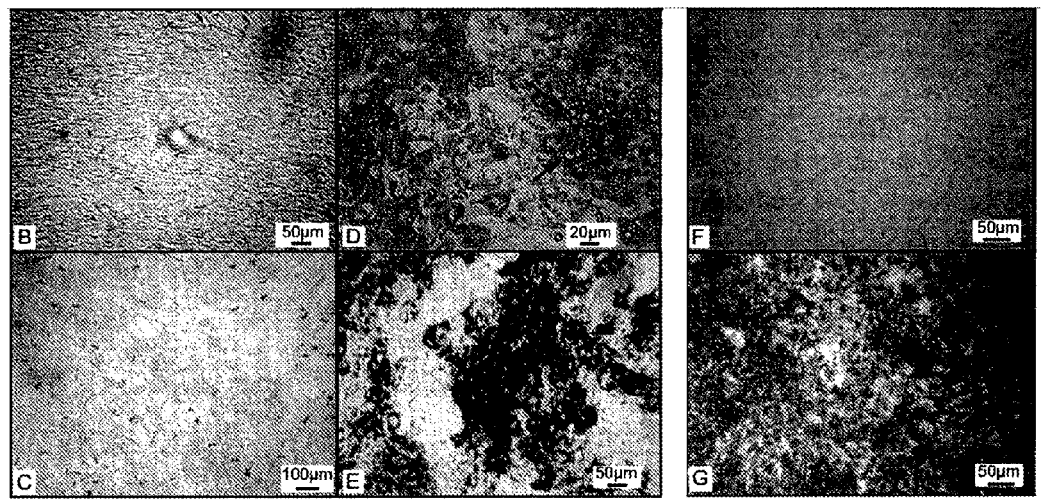
FIG. 2 shows condensation kinetic in low attachment plates. A specially treated culture dish surface is used in this 3D culture system where the cells cannot attach. A cell suspension (106 cells/ml) was supplied in low attachment plates. The cells start immediately to interact with each other after the induction of the 3D culture; (one representative experiment is shown, n=6)
Figure 2:
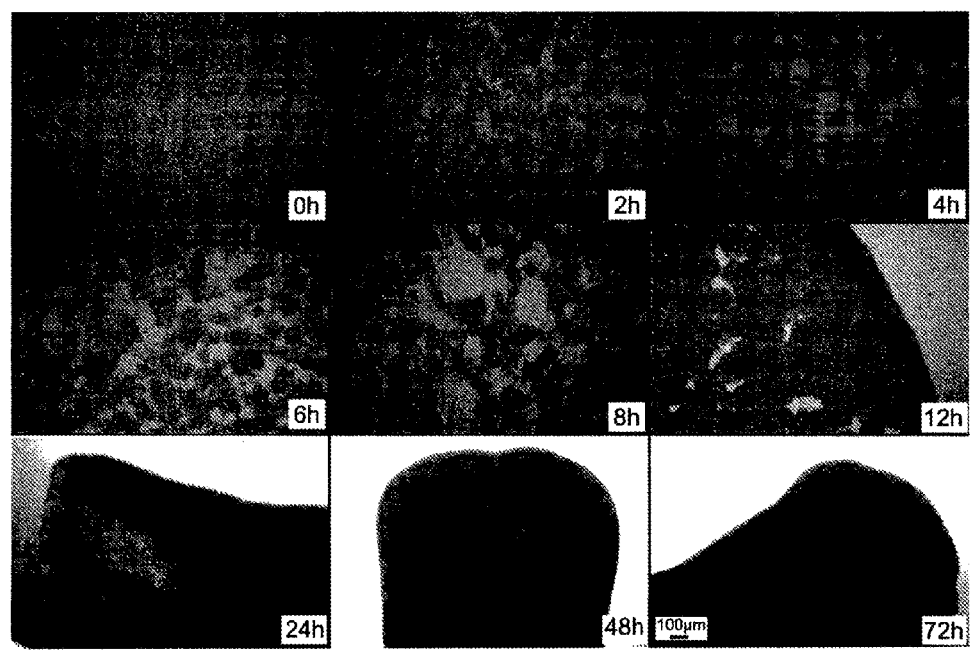

The basic idea of this culture technique is to avoid cell attachment to the culture dish surface and to maintain cell mobility. In order to prevent the formation of an attached monolayer culture cells were seeded in wells of low attachment plates with a specially treated surface. Within few hours cells started to adhere to each other resulting in a reticular structure. In the course of the following 72 hours the meshed structure condensed and finally resulted in one high-density cell aggregate per well with an average of 1-2 millimeters in diameter (FIG. 2). Cellular aggregates were cultivated for further 4 weeks without any obvious changes in size or shape. The cultivation process was subdivided in an early and a late stage and was evaluated individually.

In Vitro Mesenchymal Condensation—the Early Events

Figure 3:
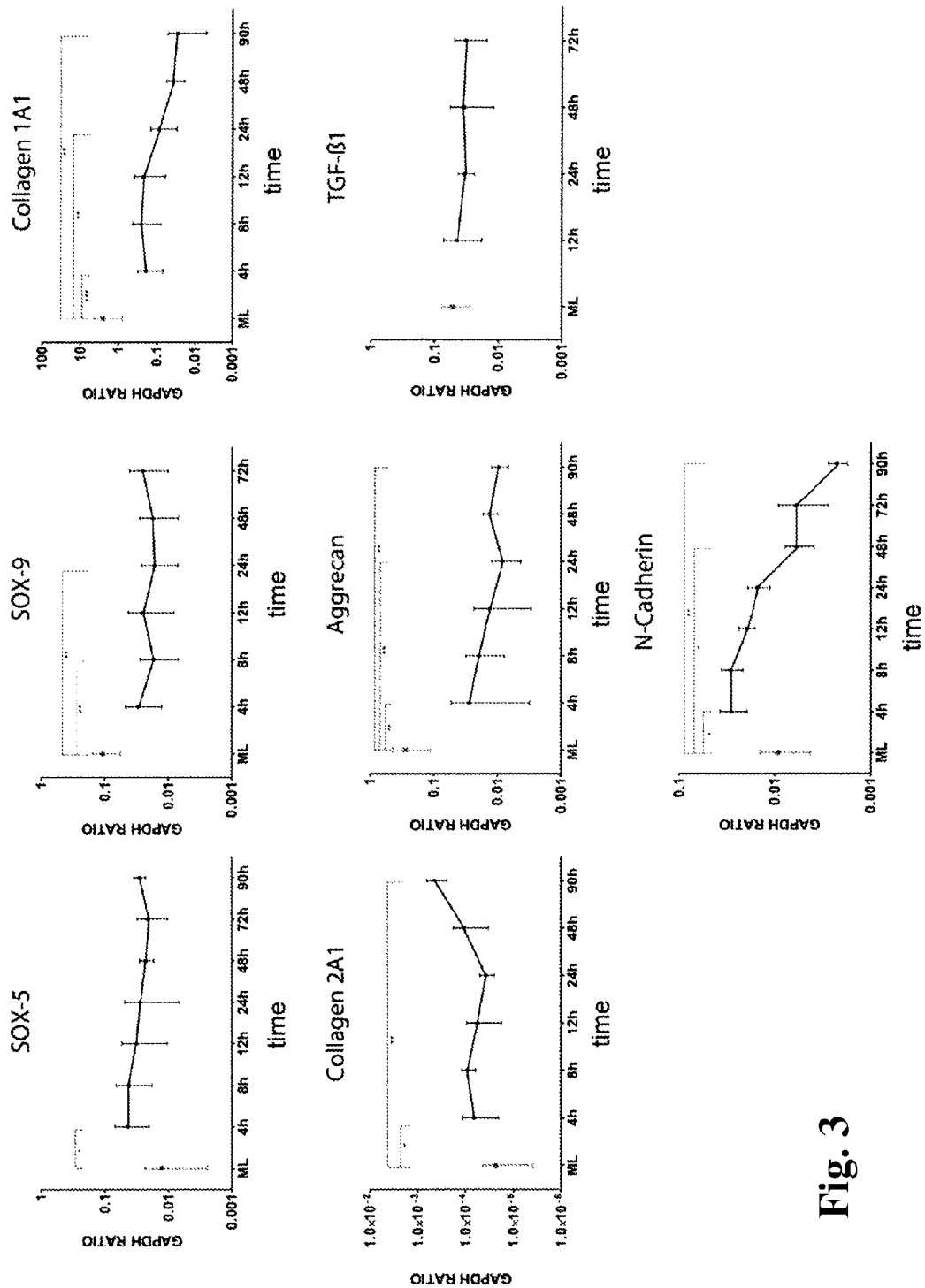
FIG. 3 shows gene expression kinetic of chondrogenesis relevant genes during the condensation stage. Real Time PCR analysis of gene expression within the first 90 or 72 hours after 3D culture induction compared to monolayer expression. Housekeeping gene ratios are presented in logarithmic scale, (n=6) statistical analysis by Mann-Whitney U_-test.

In the first step, the expression of genes characteristic for chondrogenic differentiation was analyzed (FIG. 3). The mRNA levels of the transcription factor SOX-5 were slightly up regulated after 12 hours of cultivation. At later points in time the expression dropped back to monolayer levels. Surprisingly, the transcriptional regulator SOX-9 was found to be down regulated 3-fold compared to monolayer cultures. This decreased mRNA level was maintained within the first three days in condensation formation. Nevertheless, both transcription factors were highly expressed both in monolayer and low attachment cultures indicated by the GAPDH ratio. Dedifferentiated chondrocytes showed a distinct TGF-β1 expression; however, this growth factor remained unchanged in cellular condensation. As expected, N-Cadherin expression was significant up regulated in low attachment condensations within the first hours of condensation. At later points in time, when the condensate has been formed, a 4-fold diminished gene expression was detected for the adhesion molecule. Surprisingly, significant changes in mRNA levels for the selected matrix molecules were measured even in the initial phase of the 3D cultivation. Collagen type 1A1 was found to be abundantly expressed in monolayer culture, but, this molecule was down regulated 10-fold 4 hours after 3D culture induction and showed further stepwise decrease within the next 90 hours. In contrast, expression of the cartilaginous matrix molecule Collagen type 2A1 was found to be induced 12-fold after 90 hours of low attachment culture. The mRNA level for the proteoglycan component Aggrecan was, however, substantially reduced by factor 10 at very early points in time (4 hours) and further decreased within the next 4 days of 3D culture (FIG. 3).

Chondrogenic Differentiation—The Late Events

Figure 4:
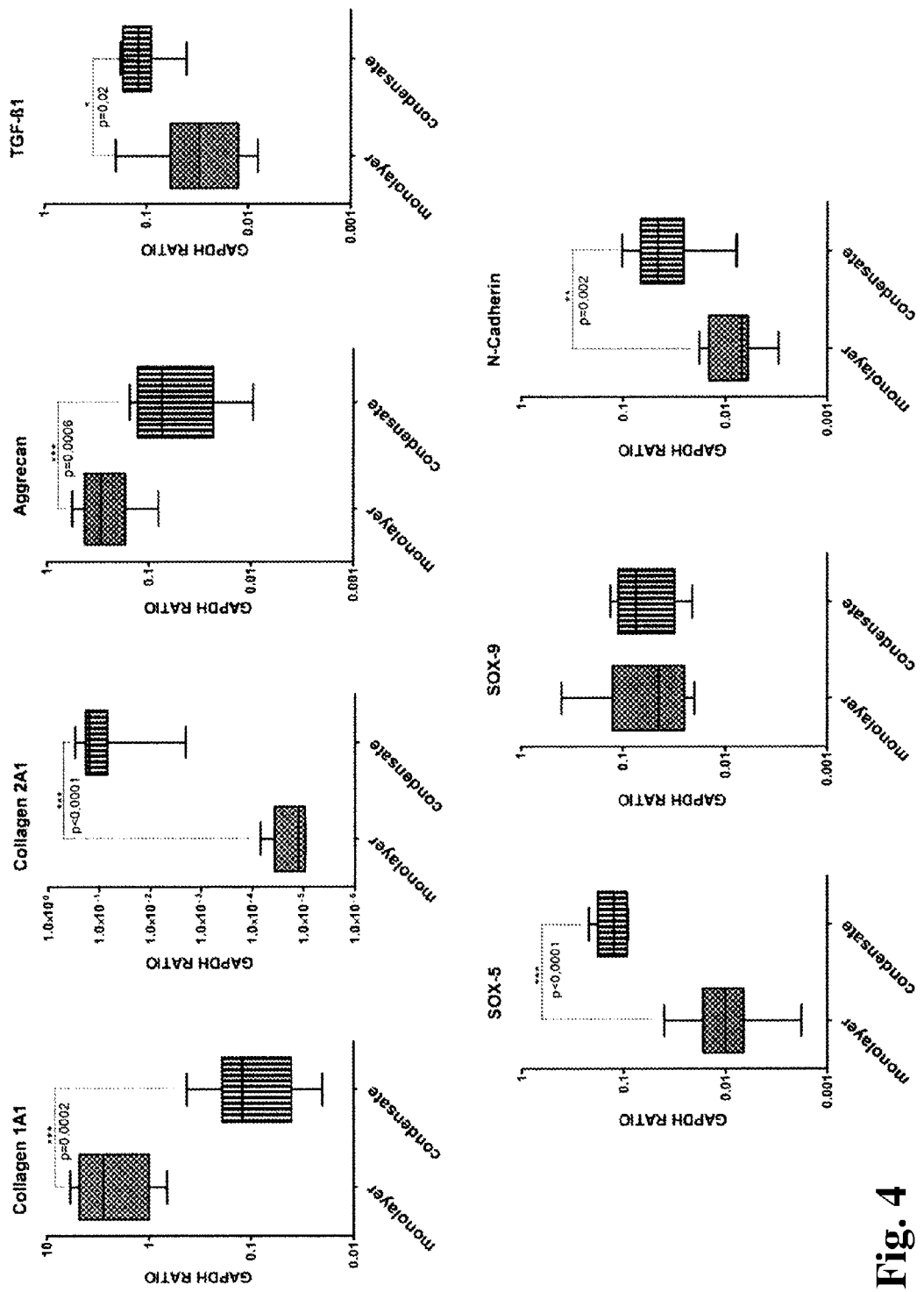
FIG. 4 shows gene expression of chondrogenesis relevant genes after 28 days of low attachment culture. Real Time PCR analysis of gene expression 28 days after 3D culture induction compared to monolayer expression. Housekeeping gene ratios are presented in logarithmic scale, (n=6) statistical analysis by Mann-Whitney U_-test.

In order to analyze the chondrogenic potential of the low attachment 3D culture system accumulation of specific extracellular matrix components were defined (FIG. 4). Furthermore, the expression of chondrogenesis associated genes were quantified by real time PCR (FIG. 4). After 28 days aggregates were sectioned for histological analysis. Hematoxylin staining of aggregate sections demonstrated a high cellular density. Moreover, a massive accumulation of extracellular matrix proteoglycans could be observed by Alcian Blue staining. The increase of Collagen type 2A1 expression by 3 orders of magnitude after 4 weeks of 3D culture was the most outstanding result for the determined matrix molecules. A kinetic immunohistological analysis for Collagen type 2A1 expression demonstrated an accumulation of Collagen type 2A1 even during the initial phase of 3D culture. Within the first two days after culture induction no Collagen 2A1 signals could be detected. However, 8 days after induction of cell condensation a considerable signal, and, after four weeks of culture an even more extensive deposition of Collagen type 2A1 was evident. Furthermore, a reduction of Collagen type 1A1 expression was evident by a 25-fold reduction of mRNA level compared to monolayer cultures. Unexpectedly, the Aggrecan mRNA level was reduced 5-fold in comparison to proliferative 2D cultures (FIG. 4). Surprisingly, the transcription factor Sox-9 exhibited an exceptional high level of gene expression in proliferating monolayer cells indicated by GAPDH ratios. After the transient decrease of expression during the aggregate formation, the mRNA level returned to monolayer basic values. On the other hand, a further gain in expression for Sox-5 by factor 14 could be detected. The relative expression of Sox-5 was thus in excess of relative Sox-9 expression after 4 weeks of low attachment culture. A further increase in the mRNA levels of TGFβ1 and the adhesion molecule N-Cadherin could additionally be determined in 3D culture (FIG. 4).

Comprehensive Analysis the Condensation and Differentiation Process

Figure 5:
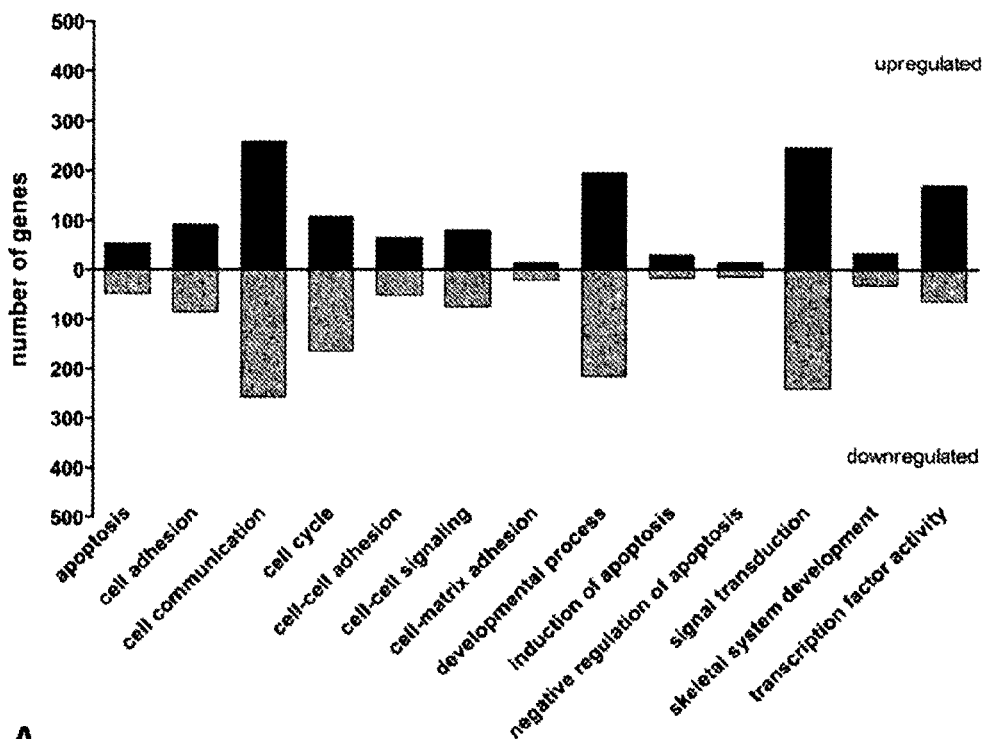
FIG. 5 shows classification of differentially expressed genes. Evaluation of two independent microarray experiments for [A] condensation stage (24 h) and [B] differentiated stage (28 days), respectively. Numbers of upregulated and downregulated genes in selected gene ontology groups are shown according to Panther gene ontology database.
Figure 5:
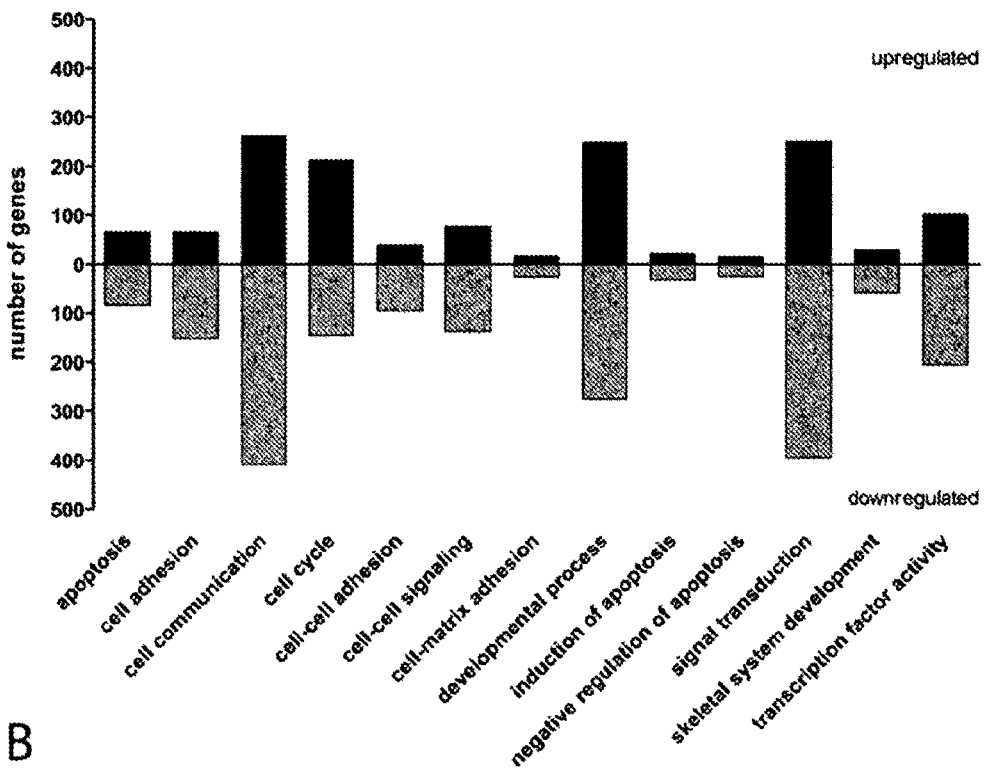

In order to make use of the scaffold free differentiation system genome wide microarray analysis was employed for further investigations of cell differentiation as well as to characterize changes in expression pattern during of the condensation process. Two independent experiments with individual primary cell cultures were performed. The fluorescent labelled probes were hybridized on Agilent 44K DNA chips. The resulting data of both chips were merged for evaluation. Genes were designated to be regulated genes if both arrays demonstrated at least a 2-fold change in gene expression. The p-value cut-off was pre-assigned to p<0.05. In order to get a general idea of this particular investigated biological process, regulated genes were grouped according the Panther GO classification (Table 1-5). The groups with the highest number of regulated genes in both the early and the late phase are cell-cell communication, developmental process and signal transduction (FIG. 5), indicating a massive modulation of gene expression in functional groups that are required to induce differentiation processes. The aim of the 3D culture system, however, is the redifferentiation of dedifferentiated chondrocytes. Accordingly, the Panther classification "skeletal system development" was inquired in more detail.

Condensation Phase

As Table 1 and 2 indicate the growth factors TGF-β3 and GDF-15 as well as the transcription factor Fos are the highest up regulated genes in this classification group. Conspicuously, the expression of several members of the Hox-A cluster were defined to be elevated during the condensation stage. The TGF-β group member Inhibin-_B represents the strongest down regulated gene and the repression was evident after 28 days of culture as well.

Aggregates after 28 Days (Tables 3 and 4).

The most prominent up regulated genes after 28 days are the cartilage related matrix molecules Collagen II, IX and XI. The matrix Gla-protein and the cartilage acidic protein also show increased mRNA levels, while unexpectedly but in agreement with Real time PCR data, Aggrecan and the Aggrecan synthesizing enzymes HAS appeared to be down modulated. Among the highest up regulated genes in this classification group are the transcription factors Fos and Runx2 as well as the growth factor GDF-15, while the non cartilage matrix molecules Collagen I and XII were strongly decreased.

The Condensation Process is Mediated by Cell-Cell Adhesion

Figure 6:
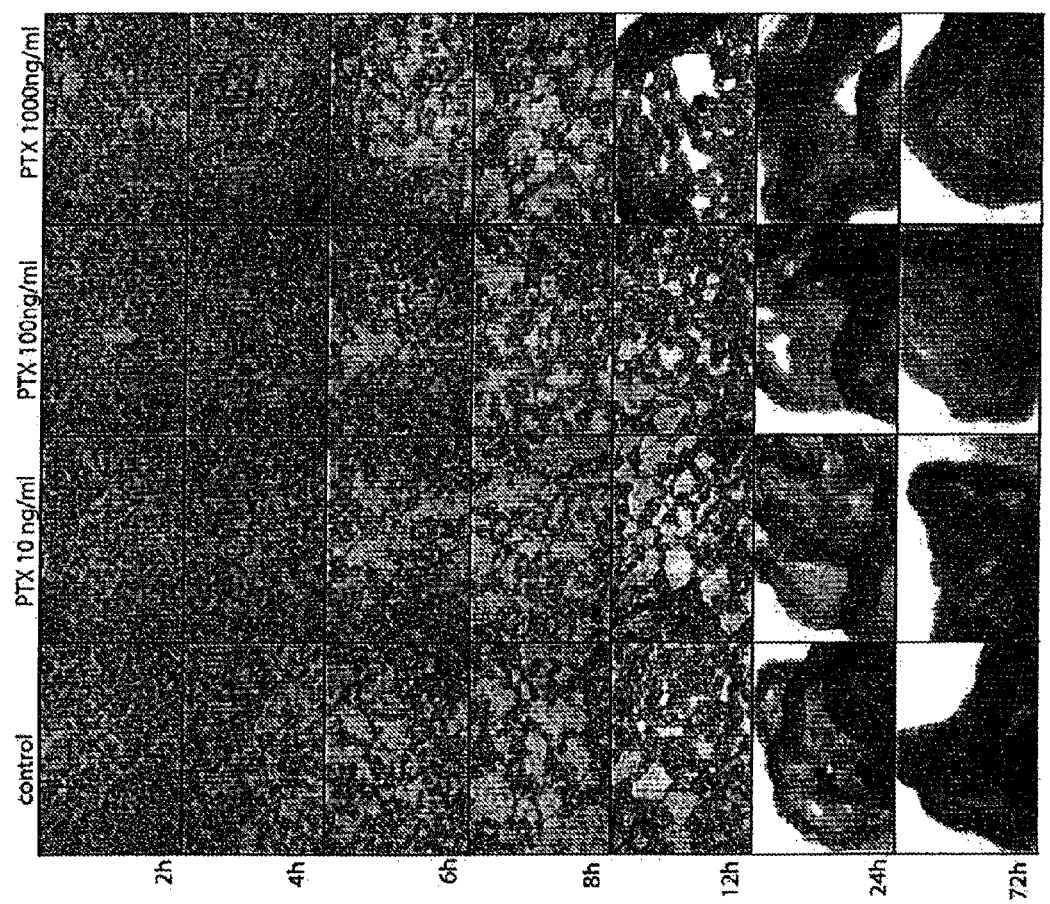
FIG. 6 shows cellular condensation of PTX treated cells. Pertussis Toxine was administered at three different concentrations to dedifferentiated chondrocytes during the condensation process. No significant changes were observed upon PTX treatment in term of condensation behavior (one representative experiment is shown, n=3)
Figure 7:
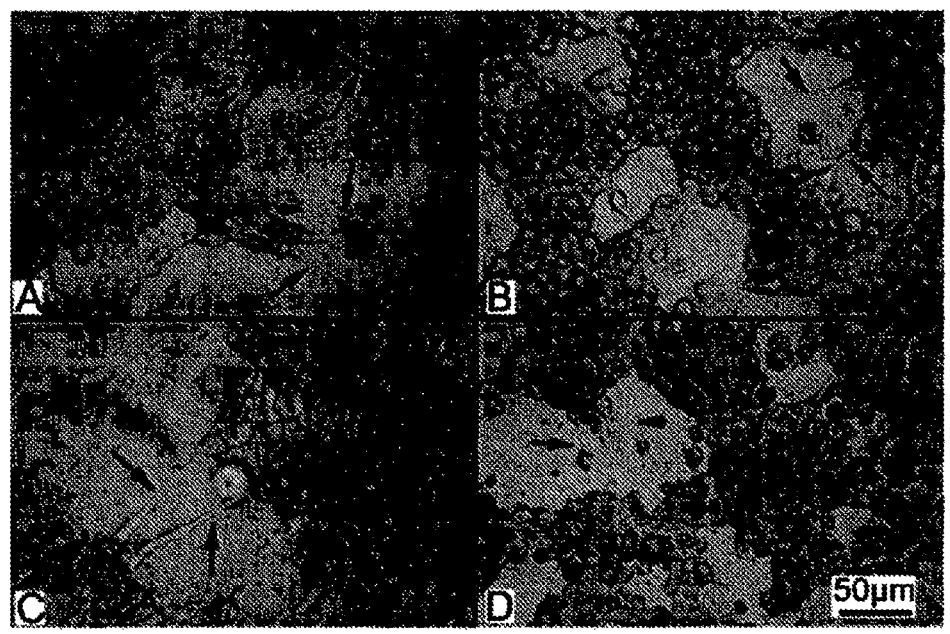
FIG. 7 shows cellular interaction and sub-aggregate connection during the condensation process. Condensation induced by 3D low attachment culture; reticular connections are visible 12 hours after culture induction; (one representative experiment is shown, n=6)

The process of mesenchymal condensation is characterized by aggregation of loose mesenchyme. Nevertheless, little is known about how this increase of progenitor cell density is mediated. Due to multifunctionality of several protein families in the Panther classification, adhesion molecules and chemotactic molecules were sub grouped in narrower sense according the KEGG database. Since DNA microarray data demonstrated differentially expressed chemokines and corresponding receptors (Table 5), the first attempt to make use of this 3D culture system, potential involvement of chemokines and migratory cellular activity should be analyzed during the condensation process. The vast majority of chemokine receptors are part of the seven transmembrane receptor family. This class of proteins elicits their signaling by G-protein coupled signal transduction. Pertussis toxin (PTX, *Bordetella pertussis*) disrupts this pathway by ADP-ribosylation of the Gα subunit the heterotrimeric G protein complex. In order to abrogate chemokine activity during condensation, low attachment culture experiments were conducted with addition of PTX in different concentrations. Unexpectedly, cell condensations of the PTX treated cultures appeared to be undistinguishable from the control experiment within the first 72 hours independent of the applied concentration (FIG. 6). Immediately after culture induction, cells formed small cell clusters, further densified via the netlike transitional stage, until finally one high-density cell aggregate was shaped independent of PTX administration and with similar kinetics. This observations indicate that chemokine mediated cell migration is not involved in the cell aggregation process. Interestingly, the results from microarray evaluations demonstrated that 75% of the differentially expressed adhesion molecules appeared to be up regulated suggesting an increased intercellular interaction during the condensation step (Table 5). This assumption was confirmed by more detailed microscopic observations. At a distinct transitional stage of occurrence of multiple sub-aggregates, long dendrite like cellular outgrowth became visible. The connections were either formed directly from one cellular sub-center to the next (FIG. 7 A-C) or established by a single cell with two extensions in opposite directions (FIG. 7 D). In later stages these thin strings are used to connect all sub-aggregates into the final aggregate. The condensation process is thus forced rather by increased expression of adhesion molecules resulting in augmented cellular interaction than chemokine mediated cell migration.

In Brief

Application of autologous progenitor cells represents a promising strategy to restore damaged cartilage tissue in osteoarthritis. These cells can be triggered to undergo differentiation into functional active chondrocytes resulting in newly synthesized cartilage. So far, several culture systems have been established for this purpose. Since chondrogenic differentiation is initiated by the step of mesenchymal condensation in vivo, it is of great interest to fully characterize the first lineage specific step in vitro. Therefore, a scaffold free low attachment 3D culture system was developed imitating the entire process of chondrogenesis including the initial condensation stage. The culture system is capable to induce chondrogenic differentiation indicated by increased gene expression of the key transcription factor Sox-5 and Collagen type II and IX. Compared to other established 3D culture systems the use of low attachment plates culture provides the advantage to analyze different phases of cell aggregation starting from a single cell suspension of previously isolated and expanded human primary cells of mesenchymal origin. Analysis of early stages demonstrates that the condensation process is rather mediated by increased cell-cell adhesion than by chemokine signalling. The low attachment 3D culture system may thus finally help to identify the key factors that are essential for induction of chondrogenic differentiation in vivo or for in vitro generated transplants for clinical applications.

Figure 8:
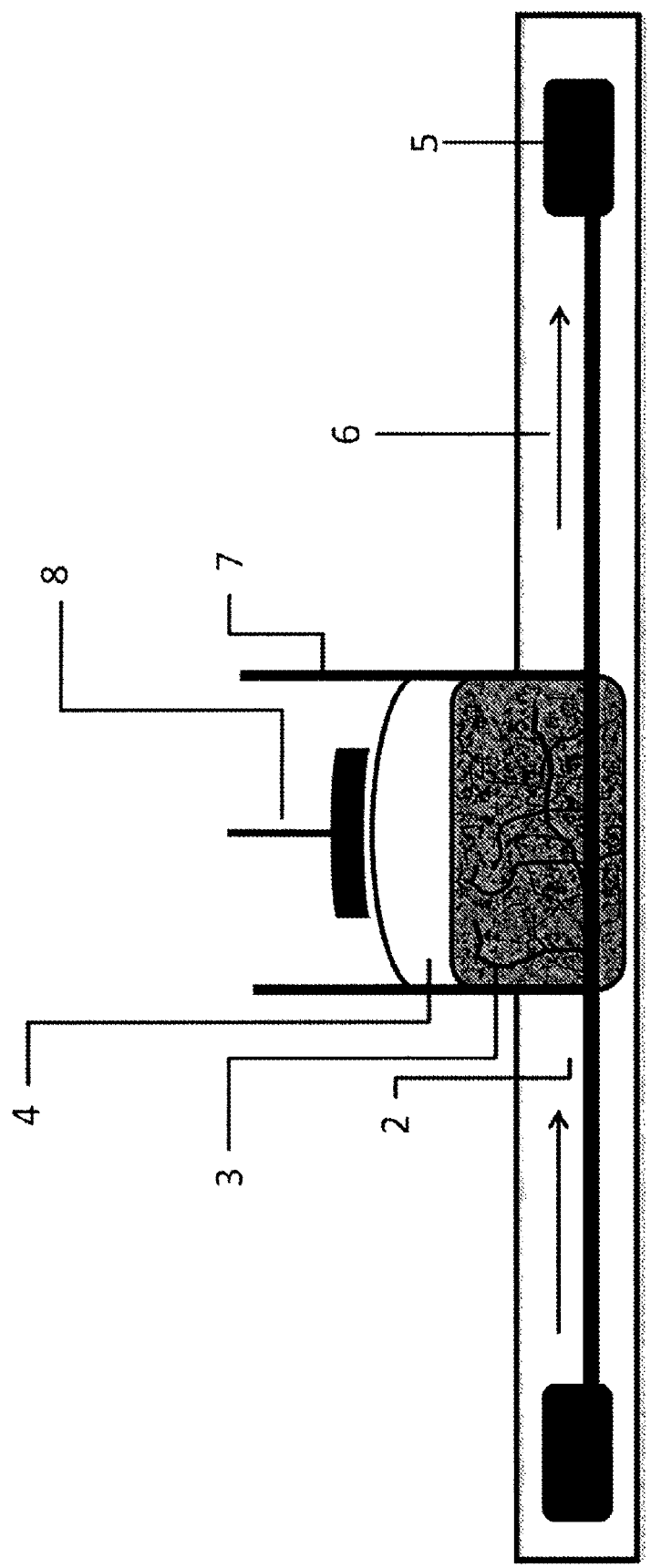
FIG. 8 shows the schematic representation of a self-contained 3D in vitro bi-phasic cartilage-bone organoid-on-a-chip device of the present invention.

III. Self-Contained 3D In Vitro Bi-Phasic Cartilage-Bone Organoid-On-A-Chip Device FIG. 8 shows a self-contained 3D in vitro bi-phasic cartilage-bone organoid-on-a-chip device of the present invention.

The self-contained 3D in vitro bi-phasic cartilage-bone organoid-on-a-chip device 1 comprises a substrate 2 wherein two medium feed reservoirs 5 are formed which are connected to each other via a medium feed channel 6. The self-contained 3D in vitro bi-phasic cartilage-bone organoid-on-a-chip device 1 further comprises a organ cavity 7 in which a 3D in vitro bi-phasic cartilage-bone organoid is housed comprising a layer of an artificial cartilage tissue 4 and a layer of an artificial bone tissue 3, wherein the artificial cartilage tissue 4 is in direct contact with a surface of the artificial bone tissue 3. In order to allow the application of mechanical forces onto the 3D in vitro bi-phasic cartilage-bone organoid, an actuator 8 may be present.

Example B

Materials and Methods

1. Isolation and Expansion of MSCs

Human MSCs were isolated from femoral head marrow, obtained after joint replacement surgery, with written consent as per the guidelines of the Ethics board of the Charité—Universitätsmedizin Berlin, as previously described. The cells were then expanded in Dulbecco's modified Eagle's media (DMEM) with 4.5 g/l glucose (PAA Laboratories, Austria) containing 10% FBS (PAA Laboratories, Austria) and Penicillin-Streptomycin (PAA laboratories). MSCs between passage 4 and 7 were used for the co-culture experiments.

2. Isolation of HSPCs

Human HSPCs were isolated from umbilical cord blood, with written consent as per the guidelines of the Ethics board of the Charité—Universitätsmedizin Berlin. Cord blood was collected in PBS-BSA-EDTA solution, and the mononuclear cells isolated by density gradient centrifugation. The HSPCs were then separated by immunomagnetic separation, using the MACS CD34+ isolation kit (Miltenyi Biotec, Germany), and following manufacturers' instructions. The freshly isolated cells were then introduced into the different culture systems at a density of $2 \times 10^4$ cells/culture.

3. Ceramics

Zirconium oxide based, hydroxyapatite coated, Sponceram HA® ceramic discs of 1 mm thickness and 1 cm diameter were purchased from Zellwerk gmbh, Germany. The discs were autoclaved prior to use.

4. Cell Culture Systems

The ceramic discs were seeded with MSCs at a density of approximately $10^6$ cells/disc, 7 days prior to seeding HSCs. The ceramic discs were submerged in DMEM—high glucose (PAA Laboratories, Austria) containing 10% FBS (PAA Laboratories, Austria) and Penicillin—Streptomycin, in ultra low attachment 24 well plates (Corning inc., USA). Plates were maintained at 37° C., 5% CO2. Media was replaced every 48 hours. Simultaneously, 6 well plates were also seeded with MSCs, so that they achieved confluency in 24 hours. One set of these plates were cultured with the same medium as the ceramics, while another was treated with osteo-inductive media containing Dexamethasone, Ascorbic acid and β-glycerophosphate (Sigma, USA). 7 days after seeding of the MSCs, freshly isolated HSPCs were introduced into 4 culture conditions: 1. 3D co-culture with MSCs seeded in the ceramic, 2. 2D co-culture with MSC monolayer seeded in 6 well plates, 3. 2D co-culture with osteo-induced MSC monolayer seeded in 6 well plates, and 4. Suspension culture in Stemspan media (Stemcell Technologies inc., Canada) supplemented with 100 ng/ml of IL-6, SCF, TPO and FLT-3L (Peprotech, UK). 9 independent MSC and HSC samples were utilized for this study. The cells from each culture system were analyzed by flow cytometry and immunohistochemistry 1, 2 and 4 weeks after start of culture. The 3D culture was analyzed at an additional time point of 8 weeks, to confirm long-term culture potential.

5. RNA Isolation, cDNA Preparation and qPCR

Isolation of RNA was performed using NucleoSpin® RNA II kit (Macherey-Nagel, Germany), following the instructions provided. Cells cultured in the ceramic were lysed directly on the ceramic. Reverse Transcription of mRNA was carried out by using TaqMan® Reverse Transcription Reagents cDNA kit (Applied Biosystems, USA), as per manufacturers' instructions. Real time PCR was performed using 1 µl cDNA with 1 µl primer mix and SensiFAST™ Sybr No-ROX kit (Bioline, Germany), in 96-well PCR plates (Biozym Scientific, Germany), and were read with Stratagene MX 3005P™ Multiplex Quantitative PCR System (Agilent Technologies, USA). Primers were ordered from TIBMolBiol (Germany).

6. Cell Tracking

For long term tracking of HSPCs and MSCs by fluorescence microscopy, the cells were labeled using Qtracker® 525 Cell Labeling Kit and CellTracker™ Red CMTPX (Invitrogen, USA), respectively, as per manufacturers' instructions, prior to culturing. To track cell division, the HSPCs were labeled with Carboxyfluorescein diacetate succinimidyl ester, (CFSE, Invitrogen, USA), at a concentration of 2.5 µM, as per manufacturers' instructions, immediately after isolation. Green labeled cells were then gated out and cell division was tracked after 1, 2 and 4 weeks, using flow cytometry.

7. Immunohistochemistry

In order to visualize the ECM and signaling molecules within the ceramic scaffolds, the ceramics with cells were fixed in Acetone (Sigma, USA) at −20° C., 2 weeks after seeding the tracked HSPCs. The discs were then cut using a scalpel and stained in 96 well plates, in a total volume of 150 µl, with primary antibodies for Collagen I (mouse α human, Sigma, USA), C-Kit (mouse α human, Santa Cruz Biotechnology Inc, USA), Fibronectin (mouse α human, Millipore, USA), Integrin 4a (mouse α human, Abcam, UK) and N-Cadherin (mouse α human, Santa Cruz Biotechnology Inc, USA). The samples were then stained with goat anti-mouse secondary antibody coupled with Alexa 350 or Alexa 594 (Invitrogen, USA), washed and visualized by microscopy.

8. Fluorescence and 2-Photon Microscopy

The presence of the Qtracker® green tracked HSPCs in the co-culture system after 1, 2, 4 and 8 weeks was confirmed by visualizing them under a digital fluorescence microscope (BZ 9000, Keyence, Germany), after counterstaining the nuclei with DAPI (Sigma, US). The ECM and signaling molecules were visualised as 3D stacks using a 2 photon microscope (Trimscope II, LaVision BioTec, Germany), and rendered using Imaris version 7.5 (Bitplane Scientific Software, Switzerland).

9. Scanning Electron Microscopy (SEM)

SEM was used to visualize the structural similarity between the cell-seeded ceramic culture system and bone marrow, and also the physical interaction on HSPCs and MSCs. Ceramic discs with MSCs and HSPCs, after 2 weeks of co-culture, and 1 cm² pieces of bone marrow excised from femoral heads were fixed and dehydrated using acetone and prepared by critical point drying. These samples were then coated with gold and silver, and visualized using a Hitachi S-520 SEM (Hitachi, Japan).

10. Flow Cytometry

The phenotype of the HSPCs from all the culture systems was compared on the basis of surface marker expression, by flow cytometric analysis. Cells were collected from all the adherent culture systems by incubating with 1× Trypsin—EDTA (PAA Laboratories, Austria) for 30 minutes, at 37° C. in an incubator. The suspension cells were simply pipetted into collection tubes. The cells were then stained with the following antibodies, as per manufacturers' instructions: CD34-APC (Miltenyi Biotec, Germany), CD38-PE (eBioscience®, USA), Annexin V—Pacific Blue (BioLegend, USA), Propidium Iodide (Sigma, USA). Flow cytometry analysis was carried out using a MACSQuant® Analyzer (Miltenyi, Germany) flow cytometer and the data was analyzed using FlowJo software, version 7.6.5 (Tree Star inc., USA).

11. CFU-GEMM ASssay

Myeloid differentiation potential of HSPCs obtained from the ceramic co-culture system 1, 2, 4 and 8 weeks after seeding was tested using the colony forming unit—granulocyte, erythrocyte, macrophage, megakaryocyte assay. 1000 cells were seeded in CFU-GEMM media (Miltenyi Biotec, Germany) and the colonies visualized and scored after 2 weeks.

12. Statistical Analysis 2-way ANOVA analysis, followed by Bonferroni corrections were applied to the data sets, using GraphPad Prism® software version 5.0 (GraphPad Software Inc., USA). P values greater than or equal to 0.05 were considered significant. Data is represented as means +/−standard deviation.

Results

1. MSCs Produce a Microenvironment Bearing Close Structural Resemblance to Bone Marrow, within 7 Days of Culture in the Ceramic.

The influence of 3D culture conditions on the differentiation and ECM production in bone marrow MSCs have been extensively documented. Rigid scaffolds, such as the ceramics used in this study, have been shown to predispose MSCs to osteogenic differentiation. The effect of 3D culture in the ceramic scaffolds on the MSCs was, therefore determined prior to introduction of HSPCs.

Figure 9:
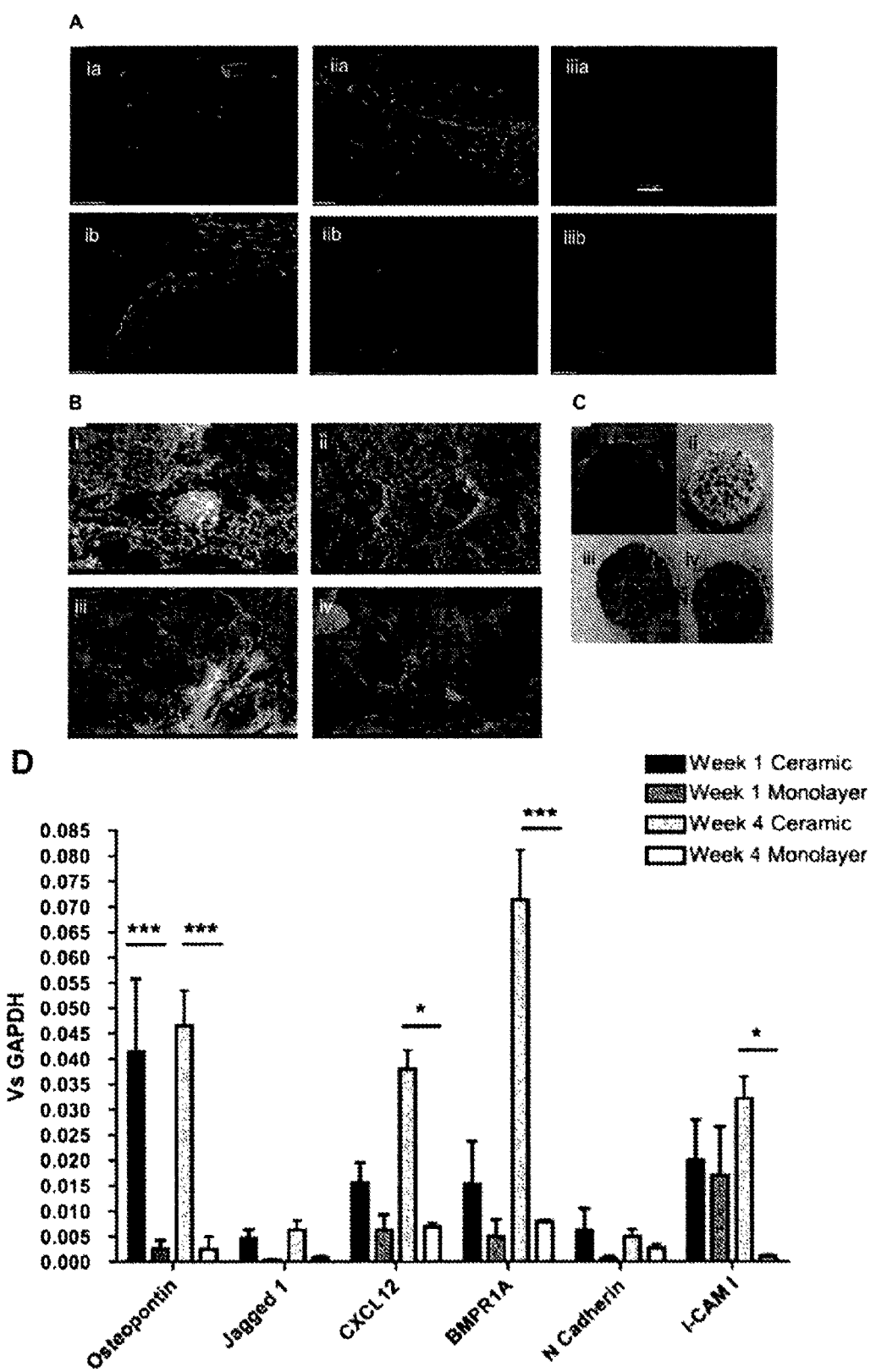
FIG. 9 shows the behavior of MSCs in 3D ceramic culture system. (A) Immunohistochemistry and 2-photon microscopy of niche ECM components. (i) Collagen-I, (ii) fibronectin and (iii) integrin 4a are highly expressed between (a) day 1 and (b) day 7 of culture. (Scale bars: 100 µm). (B) SEM imaging illustrating structural similarity between (i, iii) MSCs after 2 weeks of 3D culture and (ii, iv) bone spongiosa (Scale bars: 10 µm). (C) Spontaneous osteogenic differentiation of MSCs after 1 week of 3D culture, visualized by positive Von Kossa (i) staining and Alizarin red (iii) staining, compared to unseeded ceramics (ii, iv). (D) Real time PCR analysis of known niche molecules in the co-culture system, after 1 and 4 weeks, compared to monolayer. (n=3, Error bars: SD of mean, ***p<0.001)

Immune-histochemical analysis showed that the MSCs produce web like networks of ECM composed of Collagen I and Fibronectin, after 7 days of seeding (FIG. 9A(i, ii)), within which the MSCs are present. Integrin 4a is also produced (FIG. 9A(iii)). Collagen I and Fibronectin are known to be involved in maintenance of the HSC niche in the bone marrow, and are thought to mediate the securement of the HSPCs to the bone marrow. Integrin 4a is known to play a role in MSC-HSC interaction within the niche. Scanning electron microscopy (FIG. 9B) revealed striking similarity in the structure of the MSC-seeded ceramic (FIG. 9B (i, iii) to that of human bone marrow matrix (FIG. 9B (ii, iv)).

Positive Alizarin Red (FIG. 9C (i, ii)), Von Kossa staining (FIG. 9C (iii, iv)) indicated that MSCs seeded in the ceramic undergo spontaneous osteogenic differentiation after 7 days of culture.

Q-PCR analysis (FIG. 9D) of expression of the early osteogenic marker-Osteopontin, in comparison with monolayer cultures of MSCs, confirms at least partial spontaneous osteogenic differentiation of the MSCs. Other molecules with a putative role in the endosteal niche, namely Jagged 1, N-Cadherin, BMPR1a, ICAM1 and CXCR4 were also upregulated in the 3D culture, in comparison to monolayer, suggesting that the MSCs spontaneously produce a microenvironment, when cultured in the ceramic scaffold, which is conducive to HSC maintenance. 7 days was determined to be a suitable time point to introduce hematopoietic stem and progenitor cells into the system.

2. Primitive CD34+CD38− HSPCs are Maintained in the 3D Co-culture System, for Up to 8 Weeks.

Figure 10A:
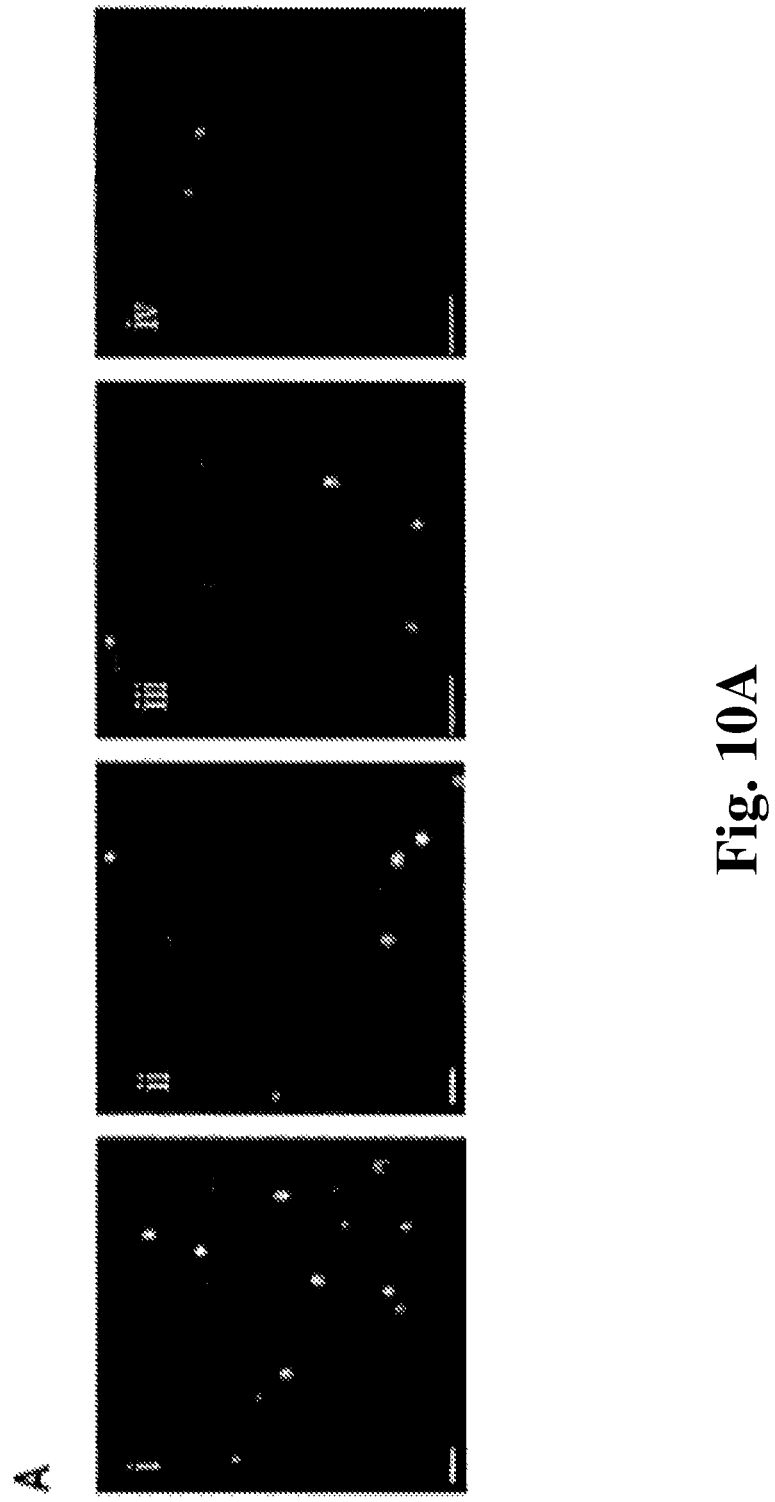
FIG. 10 shows HSPC survival and phenotype. (A) HSPCs survive in the 3D co-culture system (i) 1 week, (ii) 2 weeks, (iii) 4 weeks and (iv) 8 weeks after seeding, visualized by fluorescence microscopy. MSC nuclei are counterstained blue with DAPI. (Scale bars: 100 µm). (B) Representative FACS plots and (C, D) quantification of primitive (CD34+ CD38−) and differentiated (CD34+CD38+) HSPCs in 3D and traditional co-culture systems. (n=8, error bars—SD of mean, p<0.01, *p<0.001)

The first consideration for validating the 3D co-culture system, as a means to sustain HSPCs, was whether the HSPCs seeded into the ceramic entered into it, and remained there for significant periods of time. Using fluorescence microscopy, cell tracker-green labelled HSPCs were detected in the co-culture system 1, 2, 4 and 8 weeks (FIG. 10A) after seeding, indicating that the HSPCs infiltrate the MSC-seeded ceramics and are stably maintained for up to 8 weeks. Further time points were not tested.

Figure 10B:
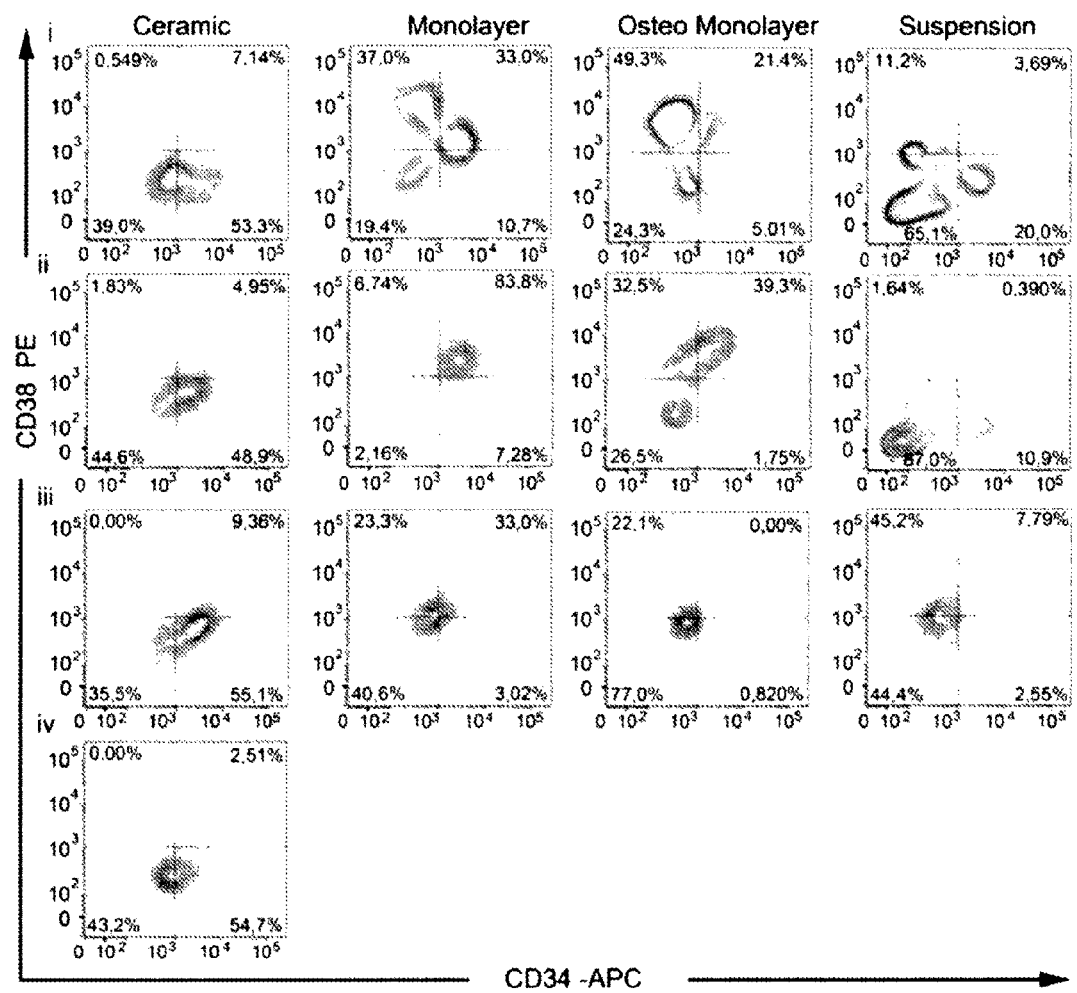

In order to determine whether the HSPCs maintained their primitive (CD34+CD38−) phenotype and explore the advantages of the 3D co-culture system over the HSPC culture strategies already in use, the percentage of primitive HSPCs maintained in the ceramic co-culture system was compared with that in traditional suspension culture and co-culture with osteo-induced and non induced MSC monolayers for up to 4 weeks, by flow cytometric detection of CD34 and CD38 expressing cells (FIG. 10B, C, D).

The percentage of CD34+, CD38− cells maintained in the ceramic co-culture system were found to remain stable at around 50% up to 8 weeks after seeding. In all the other culture conditions, however, the proportion of CD34+CD38− cells steadily decreased (FIG. 10C), until there were less than 5% primitive HSPCs. A large percentage of HSPCs (about 50%) in the monolayer co-cultures were found to be differentiating (CD34+CD38+) cells, which were not detected after 2 weeks. A small percentage (<5%) of these cells was also consistently observed in the 3D system (FIG. 10D).

3. HSPCs Maintained in the Ceramic-based Co-culture System are Slow-dividing and Quiescent.

Next, the proliferation of HSPCs in the 3D co-culture system was compared with the conventional culture methods mentioned earlier, by flow cytometric analysis of CFSE labelled HPSCs at week 1, 2 and 4. Cells that had undergone 1 or less divisions (the first 2 peaks from right in the CFSE histogram) were considered as slow proliferating, while all other cells were considered to be fast proliferating.

Figure 11A:
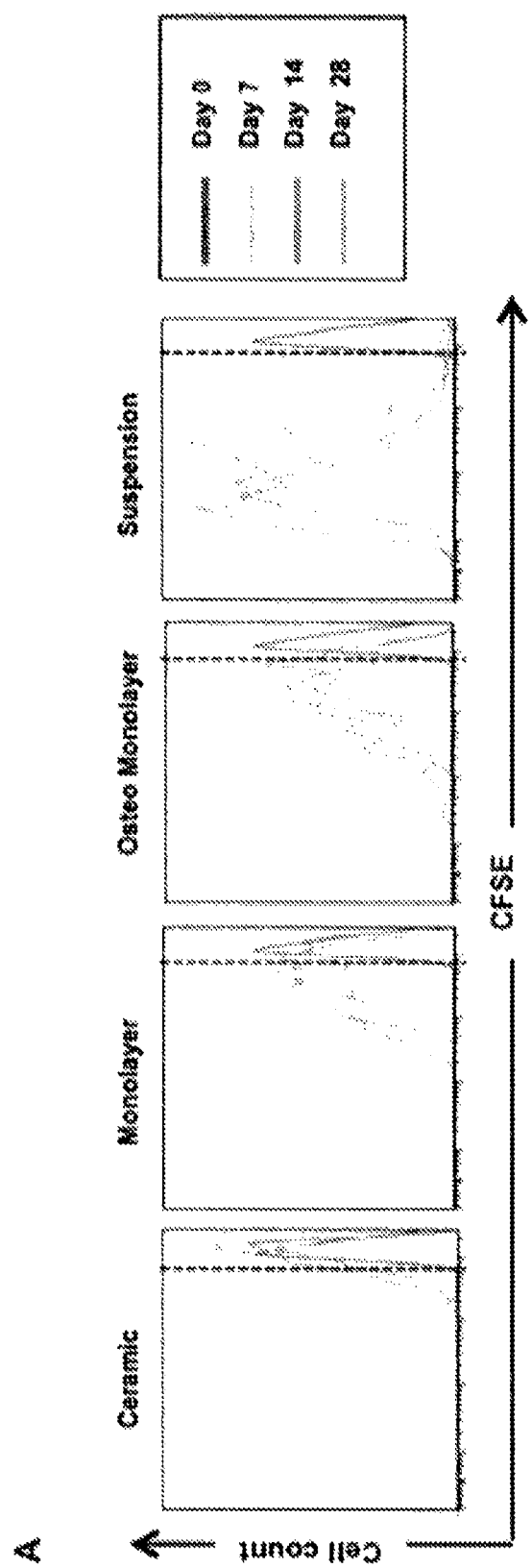
FIG. 11 shows HSPC proliferation. (A) Representative histograms of CFSE-FACS analysis showing the differential proliferation of HSPCs in the different culture systems. Dotted lines delineate the slow (right) and fast (left) proliferating cell fractions. (B) Quantification of slow proliferating cells in the four culture systems. (C, D, E) Quantification of primitive (CD34+CD38−) HSPCs in slow and fast proliferating cell fractions in each culture system, after 1, 2 and 4 weeks of culture. (n=6, error bars—SD of mean, *p<0.05, ***p<0.001)

Flow cytometry analysis and the subsequent generation of histograms (FIG. 11A) indicated that the cells in the 3D co-culture system are the slowest proliferating of all culture systems. A large proportion (>70%) of the HSPCs in the 3D co-culture were found to be slow proliferating cells. This percentage was found to decrease marginally (<10%) between weeks 2 and 4 (FIG. 11B). The proportion of slow proliferating cells was found to be relatively lower in all the conventional cultures than the 3D co-culture system, and decreased to fewer than 10% by 4 weeks of culture (FIG. 11B).

On investigating the phenotype of the slow and fast proliferating HSPCs after 1, 2 and 4 weeks of culture, by flow cytometric analysis of CD34 and CD38, it was found that the HSPCs from the 3D co-culture system retained the largest proportion of cells with the primitive CD34+CD38− phenotype (FIG. 11C, D, E) after 1, 2 and 4 weeks of culture. Over 50% of slow and fast proliferating HSPCs from the 3D co-culture retained the primitive phenotype for up to 4 weeks.

The proportion of CD34+CD38− cells in the fast proliferating cells was less than that in the slow proliferating cells, as expected. The percentage of primitive cells in the slow and fast proliferating fractions, from the traditional co-cultures, steadily decreases with time (FIG. 11C, D, E).

4. HSPCs Maintained in the Ceramic-based Co-culture System are Viable and Nonapoptotic.

Having established that the primitive HSPC phenotype is best maintained in the 3D culture, the viability of the cells was determined by measuring the expression of Annexin V—a widely used indicator of early apoptosis, and propidium iodide (PI), which is taken up by late apoptotic and necrotic cells, in all the culture systems.

A very small proportion (<0.2%) of the HSPCs in the 3D co-culture system express Annexin V (FIG. 12C), and take up PI (FIG. 12B), up to week 2, after which these cells are no longer present.

Figure 12A:
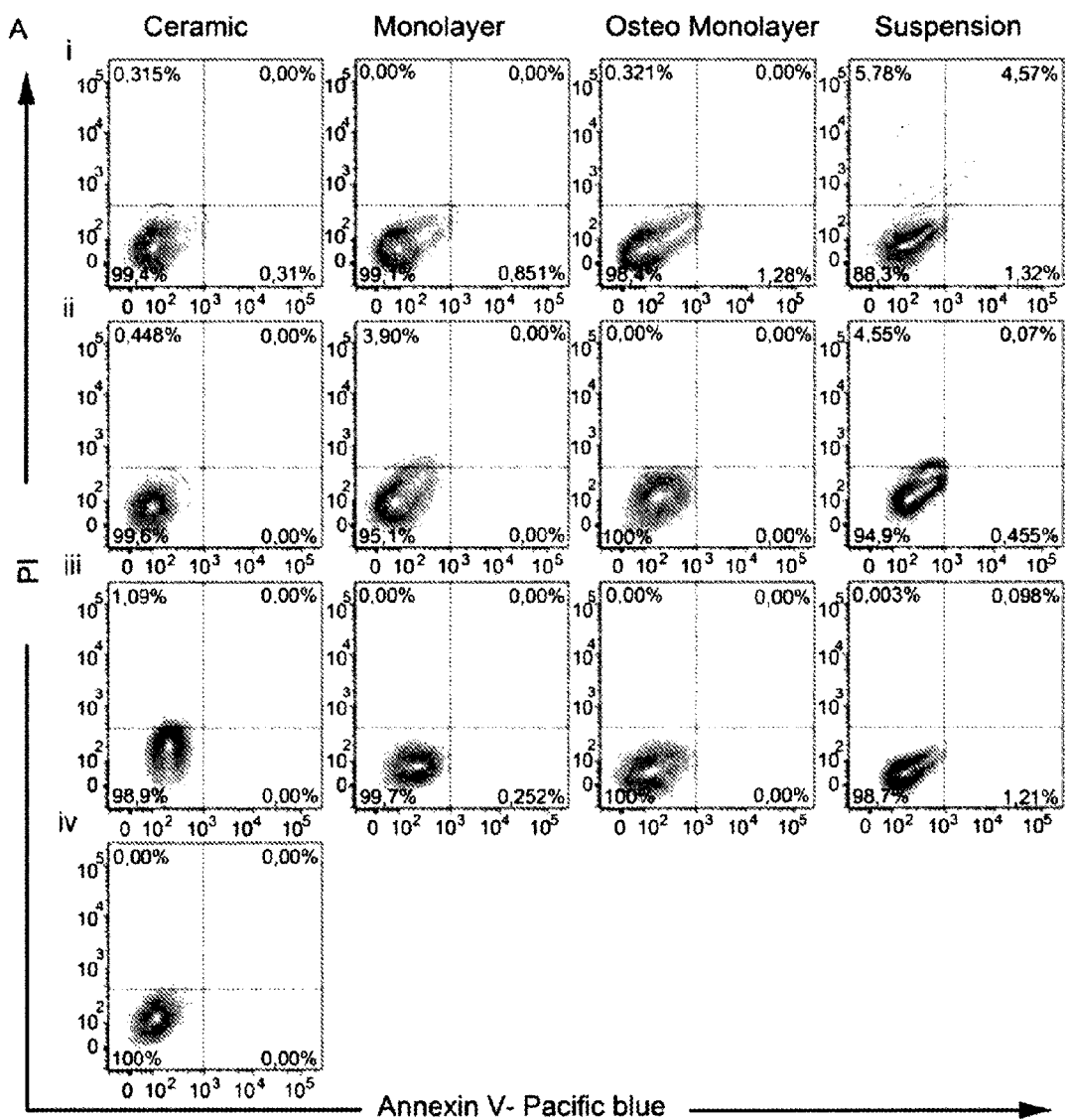
FIG. 12 shows HSPC viability and functionality. (A) Representative FACS plots and (B, C) quantification of necrotic (PI positive) and apoptotic (Annexin V positive) HSPCs in 3D and traditional co-culture systems. (n=8, error bars—SD of mean, *p<0.05 p<0.01, *p<0.001). (D,E) Multilineage differentiation potential of HSPCs from 3D co-culture system. Representative (i) GEMM, (ii) BFU-E, (iii) GM colonies and (E) scoring of colonies after CFU-GEMM assays (n=3)

In the conventional systems, particularly the suspension culture and co-culture with osteinduced MSCs, a slightly larger proportion of HSPCs (0.5-1.5%) were found to be apoptotic or necrotic (FIG. 12B,C). From this data, it was concluded that the majority of the HSPCs remain viable and non-apoptotic for up to 8 weeks, in all the culture conditions.

5. HSPCs from the Ceramic Co-culture are Functional and Capable of Multi-Lineage Differentiation.

After affirming that the HSPCs maintained in the 3D co-culture system retain their primitive phenotype and are viable, it was tested whether these cells retain the multi-lineage differentiation potential characteristic of HSPCs, using the CFU-GEMM assay.

CD34+ cells isolated from the 3D co-culture system 1, 2 and 4 weeks after seeding yielded CFU-GEMM, BFU-E and CFU-GM colonies (FIG. 12D). On counting these colonies, no significant difference was found at the different time points (FIG. 12E). The CD34+ cells thus maintained in the 3D co-culture system are not only viable, but also retain their characteristic multi-lineage differentiation potential.

6. HSPCs in the 3D Co-culture System Interact with the ECM and Cellular Components of their Microenvironment.

Finally, to illustrate that the interactions within the bone marrow HSPC niche were simulated to a great extent, within the ceramic co-culture system, physical interaction of HSPCs and MSCs within the ceramic system was investigated. Though co-localization of the HSPCs and MSCs was observed previously (FIG. 10A), no evidence of physical contact or any indication of the mechanism of interaction were obtained.

Figure 13:
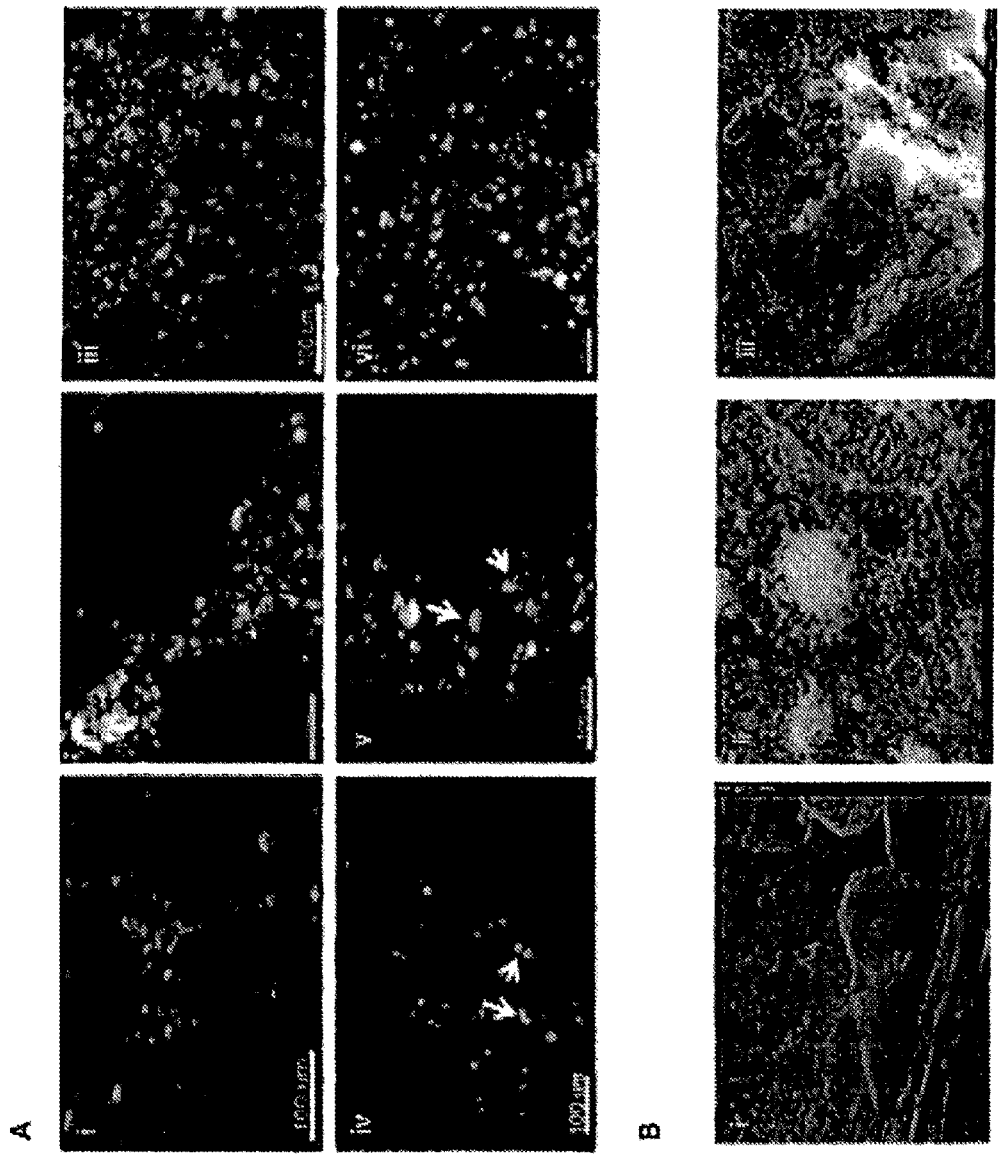
FIG. 13 shows interaction of the components in the 3D co-culture system. (A) Immunohistochemistry and 2-photon microscopy of 3D co-culture system, after 2 weeks of culture. Green tracked HSCs and red tracked MSCs are seen co-localized with Alexa 350 (blue) stained ECM components (ii) collagen I and (iii) fibronectin, as well as with the signaling molecules (iv) C-Kit (v) integrin 4a (vi) N Cadherin, when compared to the unstained control (i) (Scale bars: 100 µm). (B) SEM imaging illustrating physical interaction between the smaller, circular HSPCs and the larger, flat, adherent MSCs after 2 weeks of 3D culture (Scale bars: 10 µm).

Scanning electron microscopy (SEM) revealed that the small, rounded HSPCs, which have a diameter of about 10 μm, were always found to be in close contact with one of more flat, large MSCs, within the ceramic co-culture system (FIG. 13B). To further elucidate the factors involved in these interactions, immune-histological analyses were carried out.

2-photon microscopy revealed that fluorescent-labeled MSCs (red) and HSPCs (green) were found to be embedded in an ECM network composed mainly of Fibronectin and Collagen I (FIG. 13A ii, iii). Immunostaining of the signaling molecules C-kit, Integrin 4a and N-cadherin showed that these molecules are located in areas where HSPCs and MSCs are in contact (FIG. 13A iv, v, vi), indicating that the HSPCs and MSCs in the 3D co-culture system interact via these molecules, closely resembling the interactions thought to exist in the endosteal hematopoietic niche of the bone marrow.

Discussion

The endosteal hematopoietic niche, in which hematopoietic stem and progenitor cells (HSPCs) are maintained as slow proliferating primitive cells, is known to be a highly complex system. Several different cell types including osteoblasts, osteogenic progenitors and mesenchymal stem cells have been found to contribute to niche regulation, by a variety of mechanisms such as the production of ECM molecules, direct cell-to-cell contact, and production of signaling molecules. While individual cell types, signaling pathways and even physical criteria have been implicated in various aspects of niche maintenance, the interplay between these factors and their exact role in the niche remain unclear. The development of an in vitro model, which efficiently mimics the endosteal niche, therefore, would be of great use to investigate the interactions of the niche.

Recent research has indicated that, in order to successfully mimic the interactions within the endosteal niche, the presence of stromal support cells and 3D structure are necessary. Several independent studies have revealed that bone marrow mesenchymal stem cells (MSCs) are especially efficient in the maintenance and proliferation of primitive, quiescent HSCs in vitro. The MSCs are thought to mediate niche maintenance by production of signaling molecules like integrins, ECM components including collagen I and fibronectin, as well as by cellular interaction. Collagen I and fibronectin are known to mediate HSC homing, by binding to surface receptors and trapping secreted factors. MSCs are also known to be the precursors for osteoblastic cells, which are known partners of the HSPCs within the niche. It has been shown that the osteoblastic cells contributing to the bone marrow HSPC niche are a mixed population, comprising cells at different degrees of differentiation.

In order to simulate all these factors as closely as possible, the hydroxyapatitecoated Sponceram® 3D ceramic scaffold seeded with bone marrow MSCs was used as a culture system for cord blood derived HSPCs. The ceramic scaffolds are optimized for cell adherence and have been reported to induce spontaneous osteogenic differentiation of MSCs.

The degree of differentiation, however, was shown to be less than in cultures that were induced with BMPs or other factors, suggesting that culturing MSCs on the ceramic scaffold alone would give rise to a population of cells at different degrees of osteogenic differentiation, as in the bone marrow niche.

On immunohistochemical analysis of the ceramic seeded with MSCs, the expression of the ECM molecules—collagen I and fibronectin was observed, which comprised the main components of dense network-like structures that were observed throughout the ceramic.

Increased levels of integrin 4a were also detected. Scanning electron microscopic analysis of the MSC-seeded ceramic and bone spongiosa from the femoral head revealed a great degree of structural similarity between the two. Real time PCR analysis of this culture system showed that expression of the early osteogenic marker—osteopontin as well as molecules with known roles in the endosteal niche—Jagged-1, C-X-C chemokine receptor type 4 (CXCL12), BMP receptor 1A (BMPR1A), N-Cadherin and Intercellular Adhesion Molecule-1 (ICAM-1) were upregulated in the 3D cultures. Osteopontin is known to promote niche maintenance and quiescence of HSPCs by limiting HSPC proliferation and mobilization. Jagged-1 is thought to mediate HSPC self-renewal through Notch-signaling. CXCL12, BMPR1A and N-Cadherin have all been implicated in HSC homing, and ICAM-1 is a known mediator of intercellular binding. Within 1 week of seeding MSCs into the ceramic scaffolds, it was observed that a microenvironment bearing structural and molecular similarity to the bone marrow niche was formed. In order to complete this putative artificial niche, CD 34+HSPCs was introduced into this system.

Using fluorescence microscopy, fluorescent labeled HSPCs were detected in the 3D co-culture system up to 8 weeks after their introduction into the ceramic, indicating that the HSPCs not only enter the ceramic, but are also retained there, long term. By flow cytometric analysis, it was demonstrated that a large proportion (over 50%) of the HSPCs in the ceramic co-culture retained the primitive CD34+CD38− phenotype stably, from one week up to 8 weeks of culture. In contrast, the HSPCs cultured in conventional monolayer co-cultures or as suspension cultures in defined, cytokine—supplemented media were found to consistently lose their primitive phenotype. It was also confirmed that the cells in all the culture systems were not apoptotic or necrotic.

Since primitive HSPCs in the endosteal niche are also characterized by their slow rate of proliferation, HSPC proliferation in each of the culture systems was investigated using CFSE dilution studies. It was demonstrated that the HSPCs in the 3D co-culture system underwent very few divisions (<2) in 4 weeks, in comparison to those from the conventional cultures. The cells in the suspension culture, in particular were highly proliferative. It was also found that a larger percentage of the slowly proliferating cells from the 3D co-culture retained the CD34+CD38− phenotype.

Having thus established that the 3D co-culture system is capable of maintaining viable, slow-proliferating, CD34+ CD38− HSPCs for extended periods of time, in vitro; CFUGEMM assays were used to demonstrate that these cells are functional and capable of forming erythroid and myeloid colonies. The colony forming capacity of the HSPCs from the ceramic did not change with time in culture, indicating stable maintenance of functional HSPCs.

On examining the molecular interactions within the co-culture system, it was found that MSCs and HSPCs were located in close proximity within the fibronectin and collagen I composed network described earlier. The niche mediating molecules: Stem cell growth factor receptor (C-kit), N-Cadherin and integrin 4a were also seen to co-localize with the HSPCs and MSCs, indicating that these two cell types might interact via these molecules. C-kit is a receptor for stem cell growth factor, and is thought to promote HSC maintenance in the niche, by mediating adherence to the niche matrix. N-Cadherin and Integrin 4a are also thought to have similar roles. Further SEM imaging revealed physical interaction between the adherent MSCs and HSPCs, clearly indicating niche-like cellular interactions within the 3D coculture system.

Recent studies have succeeded in maintaining HSPCs, in 3D gel matrices composed of collagen I, and fibrin respectively, in co-culture with MSCs. These studies effectively demonstrated the need for a combination of 3D scaffolding, appropriate ECM and partner cells for the successful maintenance of HSPCs in vitro. Other work has demonstrated that osteogenic differentiated cells are potent support cells for HSPCs in 3D. Monolayer co-culture and transplantation studies have shown that MSCs highly improve HSPC maintenance both in vitro and in vivo. The 3D co-culture system combines a welldefined, rigid scaffold, bone marrow MSCs, which spontaneously produce appropriate ECM components and undergo spontaneous differentiation, and primitive HSPCs, to produce an artificial system, which closely mimics the bone marrow HSPC niche, in terms of cellular, molecular and structural composition. This system is able to sustain primitive HSPCs for longer than previously described systems.

CONCLUSION

The ceramic-based 3D co-culture system closely mimics the most important aspects of the endosteal HSPC niche, and would provide a useful in vitro model to investigate the interactions of the niche, both in healthy and diseased state. It also has great potential as a substance—testing platform, for drugs targeting any part of the niche. This system could also form the basis for an effective HSPC expansion strategy for transplantation.

TABLE 1 classification skeletal development [up regulated genes; 24 h]
Panther Class: skeletal development [ID: GO:0001501] 24 h, up regulated

| gene | description | accession | FD# 1 | FD#2 | MW |
|---|---|---|---|---|---|
| ADAMTS4 | A disintegrin and metalloproteinase with thrombospondin motifs 4 | NM_005099 | 6.7 | 5.7 | 6.2 |
| ADAMTS6 | A disintegrin and metalloproteinase with thrombospondin motifs 6 | NM_197941 | 7.8 | 2.2 | 5.0 |
| ADAMTSL4 | ADAMTS-like protein 4 | NM_019032 | 2.1 | 2.3 | 2.2 |
| ASPN | Asporin | NM_017680 | 2.7 | 4.4 | 3.5 |
| BGN | Biglycan | NM_001711 | 2.4 | 2.3 | 2.4 |
| BMP-2 | Bone morphogenetic protein 2 | NM_001200 | 3.2 | 2.1 | 2.7 |
| C1QTNF5 | Complement C1q tumor necrosis factor-related protein 5 | NM_015645 | 2.2 | 2.8 | 2.5 |
| COL11A1 | Collagen alpha-1(XI) chain | NM_080629 | 2.3 | 2.2 | 2.2 |
| COL13A1 | Collagen alpha-1(XIII) chain | NM_005203 | 2.8 | 2.4 | 2.6 |
| COL18A1 | Endostatin | NM_030582 | 4.0 | 4.2 | 4.1 |
| COL27a1 | Collagen alpha-1(XXVII) chain | NM_032888 | 4.5 | 3.2 | 3.9 |
| COL6A2 | Collagen alpha-2(VI) chain | NM_058175 | 2.1 | 2.2 | 2.2 |
| COL7A1 | Collagen alpha-1(VII) chain | NM_000094 | 8.5 | 3.8 | 6.1 |
| COLEC11 | Collectin-11 | NM_199235 | 2.4 | 2.6 | 2.5 |
| EDIL3 | EGF-like repeat and discoidin I-like domain-containing protein 3 | NM_005711 | 2.1 | 2.6 | 2.4 |
| EGFL6 | EGF-like domain-containing protein 6 | NM_015507 | 5.2 | 2.1 | 3.6 |
| FBLN1 | Fibulin-1 | NM_006486 | 2.3 | 6.3 | 4.3 |
| FBLN5 | Fibulin-5 | NM_006329 | 2.9 | 2.3 | 2.6 |
| FBLN7 | Fibulin-7 | NM_153214 | 2.9 | 2.7 | 2.8 |
| FOS | Proto-oncogene protein c-fos | NM_005252 | 14.2 | 5.4 | 9.8 |
| GDF15 | Growth/differentiation factor 15 | NM_004864 | 14.6 | 10.8 | 12.7 |
| GSC | Homeobox protein goosecoid | NM_173849 | 4.0 | 3.7 | 3.9 |
| HESX1 | Homeobox expressed in ES cells 1 | NM_003865 | 5.9 | 2.7 | 4.3 |
| HOXA13 | Homeobox protein Hox-A13 | NM_000522 | 6.0 | 7.9 | 6.9 |
| HOXA3 | Homeobox protein Hox-A3 | NM_153631 | 6.9 | 5.3 | 6.1 |
| HOXA4 | Homeobox protein Hox-A4 | NM_002141 | 4.2 | 2.2 | 3.2 |
| HOXA5 | Homeobox protein Hox-A5 | NM_019102 | 3.5 | 3.2 | 3.3 |
| HOXA6 | Homeobox protein Hox-A6 | NM_024014 | 2.1 | 2.0 | 2.1 |
| HOXB9 | Homeobox protein Hox-B9 | NM_024017 | 2.8 | 2.6 | 2.7 |
| HOXD3 | Homeobox protein Hox-D3 | NM_006898 | 2.2 | 2.4 | 2.3 |
| HSD17B8 | Estradiol 17-beta-dehydrogenase 8 | NM_014234 | 2.9 | 2.1 | 2.5 |
| LEFTY1 | Left-right determination factor 1 | NM_020997 | 3.4 | 3.7 | 3.5 |
| LMO2 | Rhombotin-2 | NM_005574 | 2.7 | 6.6 | 4.6 |
| LRIG3 | Leucine-rich repeats and immunoglobulin-like domains protein 3 | NM_153377 | 2.1 | 3.4 | 2.7 |
| LRRC15 | Leucine-rich repeat-containing protein 15 | NM_130830 | 5.2 | 2.0 | 3.6 |
| LTB | Lymphotoxin-beta | NM_002341 | 2.1 | 2.9 | 2.5 |
| LTBP3 | Latent-transforming growth factor beta-binding protein 2 | NM_021070 | 2.3 | 3.9 | 3.1 |
| LTBP4 | Latent-transforming growth factor beta-binding protein 4 | NM_003573 | 3.2 | 2.7 | 2.9 |
| MGP | Matrix Gla protein | NM_000900 | 2.4 | 4.2 | 3.3 |
| NRXN2 | Neurexin-2-alpha | NM_138732 | 2.9 | 2.1 | 2.5 |
| NRXN3 | Neurexin-3-alpha | NM_004796 | 13.0 | 11.9 | 12.5 |
| Papln | Papilin | NM_173462 | 4.2 | 4.3 | 4.3 |
| PDLIM3 | PDZ and LIM domain protein 3 | NM_014476 | 2.3 | 7.9 | 5.1 |
| PODN | Podocan | NM_153703 | 3.1 | 4.9 | 4.0 |
| RHOXF1 | Rhox homeobox family member 1 | NM_139282 | 6.5 | 4.0 | 5.3 |
| RPS6KA6 | Ribosomal protein S6 kinase alpha-6 | NM_014496 | 2.5 | 2.5 | 2.5 |
| RUNX2 | Runt-related transcription factor 2 | NM_004348 | 2.8 | 3.3 | 3.0 |
| SDC2 | Syndecan-2 | NM_002998 | 2.7 | 3.1 | 2.9 |
| SHOX2 | Short stature homeobox protein 2 | NM_006884 | 2.4 | 2.1 | 2.2 |
| TGFB3 | Transforming growth factor beta-3 | NM_003239 | 14.0 | 4.2 | 9.1 |
| TNFSF10 | Tumor necrosis factor ligand superfamily member 10 | NM_003810 | 4.0 | 2.0 | 3.0 |
| TOM1 | Target of Myb protein 1 | NM_005488 | 2.4 | 2.1 | 2.3 |
| VIT | Vitrin | NM_005488 | 2.4 | 2.1 | 2.3 |
| WWP2 | NEDD4-like E3 ubiquitin-protein ligase WWP2 | NM_199424 | 4.9 | 3.1 | 4.0 |

[FD: fold change; AV: average]

TABLE 2 classification skeletal development [down regulated genes; 24 h]
Panther Class: skeletal development [ID: GO:0001501] 24 h down regulated

| gene | description | Accession | FD#1 | FD#2 | AV |
| --- | --- | --- | --- | --- | --- |
| ADAMTS1 | A disintegrin and metalloproteinase with thrombospondin motifs 1 | NM_006988 | −5.1 | −4.4 | −4.7 |
| ADAMTS5 | A disintegrin and metalloproteinase with thrombospondin motifs 5 | NM_007038 | −3.8 | −2.7 | −3.3 |
| C1QTNF2 | Complement C1q tumor necrosis factor-related protein 2 | NM_031908 | −5.2 | −5.7 | −5.4 |
| CAP1 | Adenylyl cyclase-associated protein 1 | NM_006367 | −3.4 | −2.7 | −3.0 |
| ccbe1 | Collagen and calcium-binding EGF domain-containing protein 1 | NM_133459 | −3.8 | −4.0 | −3.9 |
| CMKLR1 | Chemokine receptor-like 1 | NM_004072 | −5.8 | −2.1 | −4.0 |
| COL17A1 | 97 kDa linear IgA disease antigen | NM_000494 | −2.1 | −2.0 | −2.1 |
| COL1A1 | Collagen alpha-1(I) chain | NM_000088 | −3.4 | −2.1 | −2.7 |
| DCBLD1 | Discoidin, CUB and LCCL domain-containing protein 1 | NM_173674 | −7.3 | −2.6 | −4.9 |
| FARP1 | PERM, RhoGEF and pleckstrin domain-containing protein 1 | NM_005766 | −2.9 | −2.1 | −2.5 |
| FARP2 | FERM, RhoGEF and pleckstrin domain-containing protein 2 | NM_014808 | −2.8 | −3.2 | −3.0 |
| FBN2 | Fibrillin-2 | NM_001999 | −4.1 | −3.7 | −3.9 |
| FGD4 | FYVE, RhoGEF and PH domain-containing protein 4 | NM_139241 | −4.7 | −3.1 | −3.9 |
| FOSL1 | Fos-related antigen 1 | NM_005438 | −2.8 | −3.5 | −3.1 |
| HECW2 | E3 ubiquitin-protein ligase HECW2 | NM_001017972 | −3.0 | −3.7 | −3.4 |
| HOXC8 | Homeobox protein Hox-C8 | NM_022658 | −4.7 | −4.1 | −4.4 |
| INHBB | Inhibin beta B chain | NM_002193 | −11.8 | −5.5 | −8.6 |
| KIAA0317 | Protein KIAA0317 | NM_001039479 | −2.5 | −2.6 | −2.6 |
| NOTCH1 | Notch 1 intracellular domain | NM_017617 | −2.7 | −2.7 | −2.7 |
| PTX3 | Pentraxin-related protein PTX3 | NM_002852 | −7.8 | −7.9 | −7.8 |
| RPS6KA2 | Ribosomal protein S6 kinase alpha-2 | NM_021135 | −4.1 | −3.3 | −3.7 |
| SHOX | Short stature homeobox protein | NM_000451 | −2.1 | −2.1 | −2.1 |
| SLIT2 | Slit homolog 2 protein C-product | NM_004787 | −4.4 | −3.0 | −3.7 |
| SMURF2 | E3 ubiquitin-protein ligase SMURF2 | NM_022739 | −4.7 | −11.1 | −7.9 |
| TRAF3 | TNF receptor-associated factor 3 | NM_145725 | −5.8 | −3.1 | −4.4 |
| UBE3C | Ubiquitin-protein ligase E3C | NM_014671 | −4.2 | −6.2 | −5.2 |
| ZYX | Zyxin | NM_003461 | −3.2 | −2.2 | −2.7 |

[FD: fold change; AV: average]

TABLE 3 classification skeletal development [up regulated genes; 28 days]
Panther Class: skeletal development [ID: GO:0001501] 28 days up regulated

| gene | description | Accession | FD#1 | FD#2 | AV |
| --- | --- | --- | --- | --- | --- |
| AHSG | Alpha-2-HS-glycoprotein chain B | NM_001622 | 2.7 | 2.3 | 2.5 |
| B3GALT4 | Beta-1,3-galactosyltransferase 4 | NM_003782 | 2.6 | 4.3 | 3.5 |
| COL11A1 | Collagen alpha-1(XI) chain | NM_080629 | 5.6 | 2.9 | 4.3 |
| COL11A2 | Collagen alpha-2(XI) chain | NM_080680 | 6.3 | 5.8 | 6.0 |
| COL14A1 | Collagen alpha-1(XIV) chain | NM_021110 | 2.8 | 2.4 | 2.6 |
| COL18A1 | Endostatin | NM_030582 | 5.5 | 5.8 | 5.6 |
| COL2A1 | Chondrocalcin | NM_002844 | 9.3 | 11.0 | 10.2 |
| COL9A2 | COL9A2, collagen, type IX, alpha 2 | NM_001852 | 2.1 | 2.0 | 2.0 |
| COL9A3 | Collagen alpha-3(IX) chain | NM_001853 | 22.2 | 29.2 | 25.7 |
| CRTAC1 | cartilage acidic protein 1 | NM_018058 | 2.5 | 8.8 | 5.7 |
| DLX4 | Homeobox protein DLX-4 | NM_138281 | 3.9 | 2.1 | 3.0 |
| EDIL3 | EGF-like repeat and discoidin I-like domain-containing protein 3 | NM_005711 | 3.6 | 7.1 | 5.4 |
| FBLN7 | Fibulin-7 | NM_153214 | 2.6 | 2.7 | 2.7 |
| FOS | Proto-oncogene protein c-fos | NM_005252 | 24.3 | 42.8 | 33.6 |
| FOSB | Protein fosB | NM_006732 | 4.0 | 7.3 | 5.7 |
| GDF10 | Bone morphogenetic protein 3b | NM_004962 | 4.9 | 5.1 | 5.0 |
| GDF15 | Growth/differentiation factor 15 | NM_004864 | 35.7 | 40.2 | 37.9 |
| HECTD2 | Probable E3 ubiquitin-protein ligase HECTD2 | NM_173497 | 4.0 | 2.5 | 3.3 |
| HOXA5 | Homeobox protein Hox-A5 | NM_019102 | 2.7 | 4.0 | 3.3 |
| HOXA7 | Homeobox protein Hox-A7 | NM_006896 | 2.1 | 2.3 | 2.2 |
| HOXA9 | Homeobox protein Hox-A9 | NM_152739 | 2.5 | 3.0 | 2.7 |
| HSD17B8 | Estradiol 17-beta-dehydrogenase 8 | NM_014234 | 2.7 | 2.9 | 2.8 |
| LMO2 | Rhombotin-2 | NM_005574 | 4.9 | 7.6 | 6.2 |
| MGP | Matrix Gla protein | NM_000900 | 9.3 | 6.8 | 8.1 |
| NEDD4L | E3 ubiquitin-protein ligase NEDD4-like | NM_015277 | 2.4 | 2.6 | 2.5 |

TABLE 3-continued classification skeletal development [up regulated genes; 28 days]
Panther Class: skeletal development [ID: GO:0001501] 28 days up regulated

| gene | description | Accession | FD#1 | FD#2 | AV |
|---|---|---|---|---|---|
| NKX2-1 | Homeobox protein Nkx-2.1 | NM_003317 | 2.2 | 2.7 | 2.5 |
| PAPLN | Papilin | NM_173462 | 7.3 | 3.0 | 5.2 |
| RUNX2 | Runt-related transcription factor 2 | NM_004348 | 10.0 | 7.5 | 8.8 |
| SCARA3 | Scavenger receptor class A member 3 | NM_016240 | 3.0 | 3.5 | 3.3 |
| SHOX | Short stature homeobox protein 2 | NM_006884 | 4.5 | 2.7 | 3.6 |
| SOX5 | SRY (sex determining region Y)-box 5 | NM_152989 | 7.8 | 8.0 | 7.9 |
| TNFSF10 | Tumor necrosis factor ligand superfamily member 10 | NM_003810 | 6.0 | 4.9 | 5.5 |
| UBR5 | E3 ubiquitin-protein ligase UBR5 | NM_015902 | 2.3 | 2.4 | 2.4 |
| VIT | Vitrin, ECM | NM_053276 | 9.5 | 18.3 | 13.9 |
| WWP2 | NEDD4-like E3 ubiquitin-protein ligase WWP2 | NM_007014 | 2.6 | 2.3 | 2.4 |

[FD: fold change; AV: average]

TABLE 4 classification skeletal development [do regulated genes; 28 days]
Panther Class: skeletal development [ID: GO:0001501] 28 days; down regulated

| gene | description | Accession | FD#1 | FD#2 | AV |
|---|---|---|---|---|---|
| ADAMTS1 | A disintegrin and metalloproteinase with thrombospondin motifs 1 | NM_006988 | −5.1 | −5.7 | −5.4 |
| ADAMTS2 | A disintegrin and metalloproteinase with thrombospondin motifs 2 | NM_014244 | −4.6 | −4.1 | −4.4 |
| ADAMTSL1 | ADAMTS-like protein 1 | NM_052866 | −8.0 | −7.0 | −7.5 |
| ACAN | Aggrecan | NM_013227 | −3.9 | −3.1 | −3.5 |
| C1QTNF2 | Complement C1q tumor necrosis factor-related protein 2 | NM_031908 | −3.0 | −3.0 | −3.0 |
| CCBE1 | Collagen and calcium-binding EGF domain-containing protein 1 | NM_133459 | −3.5 | −3.7 | −3.6 |
| CD248 | Endosialin | NM_020404 | −6.5 | −4.8 | −5.6 |
| CLEC3B | Tetranectin | NM_003278 | −10.6 | −4.6 | −7.6 |
| COL12A1 | Collagen alpha-1(XII) chain | NM_004370 | −13.5 | −5.9 | −9.7 |
| COL1A1 | Collagen alpha-1(I) chain | NM_000088 | −8.1 | −3.3 | −5.7 |
| COL1A2 | Collagen alpha-2(I) chain | NM_000089 | −5.2 | −2.9 | −4.0 |
| COL5A1 | Collagen alpha-1(V) chain | NM_000093 | −8.1 | −3.8 | −5.9 |
| COL8A1 | Collagen alpha-1(VIII) chain | NM_001850 | −14.5 | −6.4 | −10.5 |
| DCBLD1 | Discoidin, CUB and LCCL domain-containing protein 1 | NM_173674 | −3.4 | −3.3 | −3.3 |
| FARP1 | FERM, RhoGEF and pleckstrin domain-containing protein 1 | NM_005766 | −2.1 | −2.2 | −2.1 |
| FBN1 | Fibrillin-1 | NM_000138 | −6.4 | −3.5 | −5.0 |
| FBN2 | Fibrillin-2 | NM_001999 | −4.6 | −2.7 | −3.6 |
| FHL1 | Four and a half LIM domains protein 1 | NM_001159702 | −6.2 | −5.8 | −6.0 |
| FLRT2 | Leucine-rich repeat transmembrane protein FLRT2 | NM_013231 | −3.0 | −2.8 | −2.9 |
| GDF5 | Growth/differentiation factor 5 | NM_000557 | −7.3 | −3.3 | −5.3 |
| GPR32 | Probable G-protein coupled receptor 32 | NM_001506 | −2.9 | −2.8 | −2.9 |
| HAS1 | Hyaluronan synthase 1 | NM_001523 | −2.8 | −5.2 | −4.0 |
| HAS2 | Hyaluronan synthase 2 | NM_005328 | −8.4 | −10.7 | −9.5 |
| HAS3 | Hyaluronan synthase 3 | NM_005329 | −3.9 | −4.6 | −4.3 |
| HECW2 | E3 ubiquitin-protein ligase HECW2 | NM_020760 | −3.8 | −2.4 | −3.1 |
| HERC4 | Probable E3 ubiquitin-protein ligase HERC4 | NM_015601 | −2.9 | −2.5 | −2.7 |
| INHBB | Inhibin beta B chain | NM_002193 | −18.0 | −7.4 | −12.7 |
| LTBP2 | Latent-transforming growth factor beta-binding protein 2 | NM_000428 | −3.3 | −2.8 | −3.1 |
| PDLIM7 | PDZ and LIM domain protein 7 | NM_005451 | −3.0 | −2.3 | −2.7 |
| PTX3 | Pentraxin-related protein PTX3 | NM_002852 | −17.3 | −30.3 | −23.8 |
| SDC1 | Syndecan-1 | NM_002997 | −4.9 | −4.7 | −4.8 |
| SMURF2 | E3 ubiquitin-protein ligase SMURF2 | NM_022739 | −2.7 | −3.1 | −2.9 |
| THSD4 | Thrombospondin type-1 domain-containing protein 4 | NM_024817 | −2.3 | −2.8 | −2.6 |
| VDR | Vitamin D3 receptor | NM_000376 | −2.9 | −3.5 | −3.2 |
| ZYX | Zyxin | NM_003461 | −2.3 | −2.9 | −2.6 |

[FD: fold change; AV: average]

TABLE 5 classification skeletal development [do regulated genes; 28 days]
Panther Class: skeletal development [ID: GO:0001501] 28 days; down regulated

| gene | description | Accession | FD#1 | FD#2 | AV |
|---|---|---|---|---|---|
| ADAMTS1 | A disintegrin and metalloproteinase with thrombospondin motifs 1 | NM_006988 | −5.1 | −5.7 | −5.4 |
| ADAMTS2 | A disintegrin and metalloproteinase with thrombospondin motifs 2 | NM_014244 | −4.6 | −4.1 | −4.4 |
| ADAMTSL1 | ADAMTS-like protein 1 | NM_052866 | −8.0 | −7.0 | −7.5 |
| ACAN | Aggrecan | NM_013227 | −3.9 | −3.1 | −3.5 |
| C1QTNF2 | Complement C1q tumor necrosis factor-related protein 2 | NM_031908 | −3.0 | −3.0 | −3.0 |
| CCBE1 | Collagen and calcium-binding EGF domain-containing protein 1 | NM_133459 | −3.5 | −3.7 | −3.6 |
| CD248 | Endosialin | NM_020404 | −6.5 | −4.8 | −5.6 |
| CLEC3B | Tetranectin | NM_003278 | −10.6 | −4.6 | −7.6 |
| COL12A1 | Collagen alpha-1(XII) chain | NM_004370 | −13.5 | −5.9 | −9.7 |
| COL1A1 | Collagen alpha-1(I) chain | NM_000088 | −8.1 | −3.3 | −5.7 |
| COL1A2 | Collagen alpha-2(I) chain | NM_000089 | −5.2 | −2.9 | −4.0 |
| COL5A1 | Collagen alpha-1(V) chain | NM_000093 | −8.1 | −3.8 | −5.9 |
| COL8A1 | Collagen alpha-1(VIII) chain | NM_001850 | −14.5 | −6.4 | −10.5 |
| DCBLD1 | Discoidin, CUB and LCCL domain-containing protein 1 | NM_173674 | −3.4 | −3.3 | −3.3 |
| FARP1 | FERM, RhoGEF and pleckstrin domain-containing protein 1 | NM_005766 | −2.1 | −2.2 | −2.1 |
| FBN1 | Fibrillin-1 | NM_000138 | −6.4 | −3.5 | −5.0 |
| FBN2 | Fibrillin-2 | NM_001999 | −4.6 | −2.7 | −3.6 |
| FHL1 | Four and a half LIM domains protein 1 | NM_001159702 | −6.2 | −5.8 | −6.0 |
| FLRT2 | Leucine-rich repeat transmembrane protein FLRT2 | NM_013231 | −3.0 | −2.8 | −2.9 |
| GDF5 | Growth/differentiation factor 5 | NM_000557 | −7.3 | −3.3 | −5.3 |
| GPR32 | Probable G-protein coupled receptor 32 | NM_001506 | −2.9 | −2.8 | −2.9 |
| HAS1 | Hyaluronan synthase 1 | NM_001523 | −2.8 | −5.2 | −4.0 |
| HAS2 | Hyaluronan synthase 2 | NM_005328 | −8.4 | −10.7 | −9.5 |
| HAS3 | Hyaluronan synthase 3 | NM_005329 | −3.9 | −4.6 | −4.3 |
| HECW2 | E3 ubiquitin-protein ligase HECW2 | NM_020760 | −3.8 | −2.4 | −3.1 |
| HERC4 | Probable E3 ubiquitin-protein ligase HERC4 | NM_015601 | −2.9 | −2.5 | −2.7 |
| INHBB | Inhibin beta B chain | NM_002193 | −18.0 | −7.4 | −12.7 |
| LTBP2 | Latent-transforming growth factor beta-binding protein 2 | NM_000428 | −3.3 | −2.8 | −3.1 |
| PDLIM7 | PDZ and LIM domain protein 7 | NM_005451 | −3.0 | −2.3 | −2.7 |
| PTX3 | Pentraxin-related protein PTX3 | NM_002852 | −17.3 | −30.3 | −23.8 |
| SDC1 | Syndecan-1 | NM_002997 | −4.9 | −4.7 | −4.8 |
| SMURF2 | E3 ubiquitin-protein ligase SMURF2 | NM_022739 | −2.7 | −3.1 | −2.9 |
| THSD4 | Thrombospondin type-1 domain-containing protein 4 | NM_024817 | −2.3 | −2.8 | −2.6 |
| VDR | Vitamin D3 receptor | NM_000376 | −2.9 | −3.5 | −3.2 |
| ZYX | Zyxin | NM_003461 | −2.3 | −2.9 | −2.6 |

[FD: fold change; AV: average]

The present invention is not limited to embodiments described herein; reference should be had to the appended claims.

What is claimed is:

1. A three dimensional (3D) in vitro bi-phasic cartilage-bone organoid comprising:
   a layer of an artificial cartilage tissue; and
   a layer of an artificial bone tissue comprising a structure-giving scaffold and a bone marrow structure,
   wherein,
   the layer of the artificial cartilage tissue contacts at least one surface of the layer of the artificial bone tissue,
   the structure-giving scaffold of the artificial bone tissue comprises a 3D zirconium oxide based, hydroxyapatite coated ceramic, and
   the bone marrow structure of the artificial bone tissue comprises mesenchymal stem cells and hematopoietic stem cells prepared by a method comprising:
   seeding mesenchymal stem cells on the structure-giving scaffold,
   culturing the mesenchymal stem cell on the structure-giving scaffold for 2 to 10 days, and
   adding the hematopoietic stem cells,
   wherein the artificial cartilage tissue is prepared by a method comprising:
   providing mesenchymal progenitor cells; and
   culturing the mesenchymal progenitor cells under non-adherent conditions so as to form chondrogenic cell aggregates as the artificial cartilage tissue.

2. The 3D in vitro bi-phasic cartilage-bone organoid as recited in claim 1, wherein the artificial cartilage tissue is prepared using mesenchymal progenitor cells.

3. The 3D in vitro bi-phasic cartilage-bone organoid as recited in claim 1, wherein the artificial cartilage tissue is prepared using mesenchymal progenitor cells that comprise at least 50% of cells that are positive for a CD105 surface marker, a CD106 surface marker, a CD44 surface marker, a CD73 surface marker, a CD90 surface marker, and a CD13 surface marker, or mesenchymal progenitor cells that consist of cells that are positive for the CD44 surface marker, the CD73 surface marker, the CD90 surface marker, and the CD13 surface marker.

4. The 3D in vitro bi-phasic cartilage-bone organoid as recited in claim 1, wherein the artificial cartilage tissue is prepared from isolated primary chondrocytes.

5. The 3D in vitro bi-phasic cartilage-bone organoid as recited in claim 1, wherein the structure-giving scaffold of the artificial bone tissue consists of the 3D zirconium oxide based, hydroxyapatite coated ceramic scaffold.

6. A transplant comprising the 3D in vitro bi-phasic cartilage-bone organoid as recited in claim 1.

7. A pharmaceutical composition comprising:
   the 3D in vitro bi-phasic cartilage-bone organoid as recited in claim 1; and
   at least one pharmaceutically acceptable excipient;
or,
   a transplant comprising the 3D in vitro bi-phasic cartilage-bone organoid as recited in claim 1; and
   at least one pharmaceutically acceptable exipient.

* * * * *